US008349324B2

(12) United States Patent
Lugovskoy et al.

(10) Patent No.: US 8,349,324 B2
(45) Date of Patent: Jan. 8, 2013

(54) METHODS OF HUMANIZING IMMUNOGLOBULIN VARIABLE REGIONS THROUGH RATIONAL MODIFICATION OF COMPLEMENTARITY DETERMINING RESIDUES

(75) Inventors: Alexey Alexandrovich Lugovskoy, Woburn, MA (US); Karl Hanf, Billerica, MA (US); You Li, Newton, MA (US); Kenneth Simon, Cambridge, MA (US); Herman Van Vlijmen, Mechelen (BE)

(73) Assignee: Biogen Idec MA Inc., Cambridge, MA (US)

( * ) Notice: Subject to any disclaimer, the term of this patent is extended or adjusted under 35 U.S.C. 154(b) by 227 days.

(21) Appl. No.: 12/628,898

(22) Filed: Dec. 1, 2009

(65) Prior Publication Data

US 2010/0093980 A1 Apr. 15, 2010

Related U.S. Application Data

(62) Division of application No. 11/369,641, filed on Mar. 6, 2006, now Pat. No. 7,678,371.

(60) Provisional application No. 60/658,987, filed on Mar. 4, 2005.

(51) Int. Cl.
*A61K 39/395* (2006.01)

(52) U.S. Cl. .................................. 424/133.1; 530/387.1

(58) Field of Classification Search .................. None
See application file for complete search history.

(56) References Cited

U.S. PATENT DOCUMENTS

| 6,180,370 | B1 * | 1/2001 | Queen et al. ............... 435/69.6 |
| 6,407,213 | B1 | 6/2002 | Carter et al. |
| 6,632,927 | B2 * | 10/2003 | Adair et al. ............... 530/387.3 |
| 6,656,467 | B2 | 12/2003 | Young et al. |
| 2002/0177170 | A1 | 11/2002 | Luo et al. |
| 2003/0054407 | A1 | 3/2003 | Luo |
| 2003/0120044 | A1 | 6/2003 | Huse et al. |
| 2003/0224397 | A1 | 12/2003 | Lowman et al. |
| 2004/0010376 | A1 | 1/2004 | Luo et al. |
| 2004/0086502 | A1 | 5/2004 | Chen et al. |
| 2004/0162413 | A1 | 8/2004 | Watkins et al. |
| 2006/0122377 | A1 | 6/2006 | Dennis |

FOREIGN PATENT DOCUMENTS

| EP | 0592106 A1 | 4/1994 |
| WO | 94/16094 A2 | 7/1994 |
| WO | 02/088306 A2 | 11/2002 |
| WO | 03/002607 A1 | 1/2003 |
| WO | 03/074679 A2 | 9/2003 |
| WO | 03/099999 A2 | 12/2003 |
| WO | 2004/006955 A1 | 1/2004 |
| WO | 2004/029207 A2 | 4/2004 |
| WO | 2005/080432 A2 | 9/2005 |

OTHER PUBLICATIONS

Chen, Yvonne et al., "Selection and Analysis of an Optimized Anti-VEGF Antibody: Crystal Structure of an Affinity-matured Fab in Complex with Antigen," J. Mol. Biol., vol. 293:865-881(1999).

De Pascalis, Roberto et al, "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).

Gonzales, Noreen R. et al, "Minimizing immunogenicity of the SDR-grafted humanized antibody CC49 by genetic manipulation of the framework residues," Molecular Immunology, vol. 40:337-349 (2003).

Holm, Patrik et al., "Functional mapping and single chain construction of the anti-cytokeratin 8 monoclonal antibody TS1," Molecular Immunology, vol. 44:1075-1084 (2007).

Iwahashi, Makoto et al, "CDR substitutions of a humanized monoclonal antibody (CC49): contributions of individual CDRs to antigen binding and immunogenicity," Molecular Immunology, vol. 36:1079-1091 (1999).

Kashmiri, S.V.S. et al, "Development of a minimally immunogenic variant of humanized anti-carcinoma monoclonal antibody CC49," Critical Reviews in Oncology/Hematology, vol. 38:3-16 (2001).

Knappik, Achim et al, "Fully Synthetic Human Combinatorial Antibody Libraries (HuCAL) Based on Molecular Consensus Frameworks and CDRs Randomized with Trinucleotides," J. Mol. Biol., vol. 296:57-86 (2000).

MacCallum, Robert M. et al., "Antibody-antigen Interactions: Contact Analyais and Binding Site Topography," J. Mol. Biol., vol. 262:732-745 (1996).

Novotny, Jiri et al., "On the Attribution of Binding Energy in Antigen-Antibody Complexes McPC 603, D1.3, and HyHEL-5," Biochemistry, vol. 28:4735-4749 (1989).

Roguska, Michael A. et al., "A comparison of two murine monoclonal antibodies humanized by CDR-grafting and variable domain surfacing," Protein Engineering, vol. 9(10):895-904 (1996).

Rudikoff, Stuart et al., "Single amino acid substitution altering antigen-binding specificity," Proc. Natl. Acsd. Sci. USA, vol. 79:1979-1983 (1982).

Tamura, Midori et al, "Structural Correlates of an ANticarcinoma Antibody: Identification of Specificity-Determining Residues (SDRs) and Development of a Minimally Immunogenic Antibody Variant by Retention of SDRs Only," The Journal of Immunology, vol. 164:1432-1441 (2000).

(Continued)

Primary Examiner — Laura B Goddard
Assistant Examiner — Meera Natarajan
(74) Attorney, Agent, or Firm — Nelson Mullins Riley & Scarborough LLP; Debra J. Milasincic, Esq.

(57) ABSTRACT

The present invention is based, at least in part, on the discovery that strategic modifications of non-human donor antibody CDR residue(s) can be used to humanize antibodies. Such modifications modulate the 3D structural fit between donor antibody CDRs and human acceptor antibody framework regions that comprise the variable domains of a CDR-grafted antibody. Whereas prior art methods of humanization have relied on making framework substitutions (in which selected human framework residues are backmutated to the corresponding amino acid residue present in the non-human donor antibody), the instant invention is based, at least in part, on a method of humanizing antibodies in which selected CDR residues, and optionally adjacent FR residues, are changed in order to accommodate differences in FR amino acid sequences between donor and acceptor antibodies.

32 Claims, 6 Drawing Sheets

OTHER PUBLICATIONS

Wu, Herren et al, "Humanization of a Murine Monoclonal Antibody by Simultaneous Optimization of Framework and CDR Residues," J. Mol. Biol., vol. 294:151-162 (1999).

European Communication for Application No. 04 779 301.3, dated Jan. 29, 2008.

International Search Report for Application No. PCT/US2006/007955, dated Apr. 5, 2007.

GenBank Accession No. AAA62144.1, Leone, D.R. et al., "Humanization of an anti-alpha 4 integrin monoclonal antibody for human therapy," 2 pages, Feb. 9, 1995.

Australian Office Action for Application No. 2006220709, 3 pages, dated Dec. 6, 2010.

European Office Action for Application No. 06737167.4, 6 pages, dated Feb. 2, 2011.

Japanese Office Action for Application No. 2007-558326, 10 pages, dated Oct. 27, 2011.

* cited by examiner

Fig. 1

| | Kabat No. 2 | | | | | |
|---|---|---|---|---|---|---|
| | | | *29 | | | |
| VL muB3F6 | DFLMTQTPLSLPVSLGDQASISC | RSSQSIVHSNGNTYLE | WYLQKPGQSPKLLIY | KVSNRFS | | SEQ ID NO:3 |
| VL BAC01733 | DVVMTQSPLSLPVTPGEPASISC | RSSQSLLHSNGYNYLD | WYLQKPGQSPQLLIY | LGSNRAS | | SEQ ID NO:4 |
| VL graft B3F6 | DVVMTQSPLSLPVTPGEPASISC | RSSQSIVHSNGNTYLE | WYLQKPGQSPQLLIY | KVSNRFS | | SEQ ID NO:5 |
| VL huB3F6.v1 | DVVMTQSPLSLPVTPGEPASISC | RSSQSIVHSNGNTYLE | WYLQKPGQSPQLLIY | KVSNRFS | | SEQ ID NO:6 |
| VL huB3F6.v2 | DVVMTQSPLSLPVTPGEPASISC | RSSQSIVHSNGNTYLE | WYLQKPGQSPQLLIY | KVSNRFS | | SEQ ID NO:7 |
| VL huB3F6.v3 | DVVMTQSPLSLPVTPGEPASISC | RSSQSIVHSNGNTYLE | WYLQKPGQSPQLLIY | KVSNRFS | | SEQ ID NO:8 |
| VL huB3F6.v4 | DVVMTQSPLSLPVTPGEPASISC | RSSQSFVHSNGNTYLE | WYLQKPGQSPQLLIY | KVSNRFS | | SEQ ID NO:9 |
| VL huB3F6.v5 | DVVMTQSPLSLPVTPGEPASISC | RSSQSFVHSNGNTYLE | WYLQKPGQSPQLLIY | KVSNRFS | | SEQ ID NO:10 |
| VL huB3F6.v6 | DVVMTQSPLSLPVTPGEPASISC | RSSQSLVHSNGNTYLE | WYLQKPGQSPQLLIY | KVSNRFS | | SEQ ID NO:11 |
| VL huB3F6.v7 | DVVMTQSPLSLPVTPGEPASISC | RSSQSIVHSNGNTYLE | WYLQKPGQSPQLLIY | KVSNRFS | | SEQ ID NO:12 |
| VL huB3F6.v8 | DVVMTQSPLSLPVTPGEPASISC | RSSQSIVHSNGHTYLE | WYLQKPGQSPQLLIY | KVSNRFS | | SEQ ID NO:13 |
| | FR1 | CDR L1 | FR2 | CDR L2 | | |

| | FR3 | *93 CDR L3 | FR4 | |
|---|---|---|---|---|
| VL muB3F6 | GVPDRFSGSGSGTDFTLKISRVEAEDLGVYYC | FQGSHVPLT | FGAGTKLELK | SEQ ID NO:3 |
| VL BAC01733 | GVPDRFSGSGSGTDFTLKISRVEAEDVGVYYC | MQALQTPYT | FGQGTKLEIK | SEQ ID NO:4 |
| VL graft B3F6 | GVPDRFSGSGSGTDFTLKISRVEAEDVGVYYC | FQGSHVPLT | FGQGTKLEIK | SEQ ID NO:5 |
| VL huB3F6.v1 | GVPDRFSGSGSGTDFTLKISRVEAEDVGVYYC | FQGSWVPLT | FGQGTKLEIK | SEQ ID NO:6 |
| VL huB3F6.v2 | GVPDRFSGSGSGTDFTLKISRVEAEDVGVYYC | FQGSYVPLT | FGQGTKLEIK | SEQ ID NO:7 |
| VL huB3F6.v3 | GVPDRFSGSGSGTDFTLKISRVEAEDVGVYYC | FQGSLVPLT | FGQGTKLEIK | SEQ ID NO:8 |
| VL huB3F6.v4 | GVPDRFSGSGSGTDFTLKISRVEAEDVGVYYC | FQGSHVPLT | FGQGTKLEIK | SEQ ID NO:9 |
| VL huB3F6.v5 | GVPDRFSGSGSGTDFTLKISRVEAEDVGVYYC | FQGSWVPLT | FGQGTKLEIK | SEQ ID NO:10 |
| VL huB3F6.v6 | GVPDRFSGSGSGTDFTLKISRVEAEDVGVYYC | FQGSWVPLT | FGQGTKLEIK | SEQ ID NO:11 |
| VL huB3F6.v7 | GVPDRFSGSGSGTDFTLKISRVEAEDVGVYYC | FQGSHVPLT | FGQGTKLEIK | SEQ ID NO:12 |
| VL huB3F6.v8 | GVPDRFSGSGSGTDFTLKISRVEAEDVGVYYC | FQGSWVPLT | FGQGTKLEIK | SEQ ID NO:13 |

Figure 4. Heavy Chain Variable Regions (VH)

Figure 5. Light Chain Variable Regions (VL)

| | FR1 | CDR L1 | FR2 | CDR L2 |
|---|---|---|---|---|
| Mouse_HP1/2 | SIVMTQTPKFLLVSAGDRVTIT | CKSSQS... | AWYQQKPGQSPKLLIY | ...SNR... |
| B3 | DIVMTQSPDSLAVSLGERATINC | KSSQS... | AWYQQKPGQPPKLLIY | WAS... |
| CDR_Graft | DIVMTQSPDSLAVSLGERATINC | KSSQS... | AWYQQKPGQPPKLLIY | ...SNR... |

| | FR3 | CDR L3 | FR4 | SEQ ID NO |
|---|---|---|---|---|
| Mouse_HP1/2 | GVPDRFTGSGYGTDFTFTISTVQAEDLAVYFC | QQD... | TFGGGTKLEIK | 26 |
| B3 | GVPDRFSGSGSGTDFTLTISSLQAEDVAVYYC | QQY... | TFGQGTKVEIK | 27 |
| CDR_Graft | GVPDRFSGSGSGTDFTLTISSLQAEDVAVYYC | QQD...  | TFGQGTKVEIK | 28 |

Underline italics = Canonical Residues
Mouse_HP1/2 = Donor VL
B3 = Germline Acceptor Framework A. Murine HP1/2
B. V24A_T32V Humanized HP1/2

METHODS OF HUMANIZING IMMUNOGLOBULIN VARIABLE REGIONS THROUGH RATIONAL MODIFICATION OF COMPLEMENTARITY DETERMINING RESIDUES

RELATED INFORMATION

This application is a divisional application of U.S. patent application Ser. No. 11/369,641, filed on Mar. 6, 2006, allowed, which claims the benefit of priority to U.S. provisional patent application No. 60/658,987, filed on Mar. 4, 2005, the content of which is hereby incorporated by reference in its entirety.

The contents of any patents, patent applications, and references cited throughout this specification are hereby incorporated by reference in their entireties.

BACKGROUND OF THE INVENTION

Antibodies are naturally occurring biological agents that play a critical role in defending the body from pathogens. Antibodies, which are also commonly referred to as immunoglobulins, contain four polypeptides: two longer polypeptides ("heavy chains") that are identical to one another and two shorter polypeptides ("light chains") that are identical to one another. The heavy chains are paired with the light chains by disulfide bonds, and the two heavy chains are similarly bound to one another to create a tetrameric structure. Moreover, the heavy and light chains each contain a variable domain and one or more constant regions: the heavy chain includes one variable domain ($V_H$) followed by three constant regions ($C_H1$, $C_H2$, and $C_H3$), and the light chain includes one variable domain ($V_L$) followed by a single constant region ($C_L$).

The variable domains of each pair of light and heavy chains form the site that comes into contact with an antigen. Both $V_H$ and $V_L$ have the same general structure, with four framework regions (FRs), whose sequences are relatively conserved, connected by three hypervariable or complementarity determining regions (CDRs) (see Kabat et al., In "Sequences of Proteins of Immunological Interest," U.S. Department of Health and Human Services, 1983; see also Chothia et al., *J. Mol. Biol.* 196:901-917, 1987). The four framework regions largely adopt a β-sheet conformation and the CDRs form loops connecting, and in some cases forming part of, the β-sheet structure. The CDRs of $V_H$ and $V_L$ are held in close proximity by the FRs, and amino acid residues within the CDRs bind the antigen. More detailed accounts of the structure of variable domains can be found in Poljak et al. (*Proc. Natl. Acad. Sci. USA* 70:3305-3310, 1973) Segal et al. (*Proc. Natl. Acad. Sci. USA* 71:4298-4302, 1974), and Marquart et al. (*J. Mol. Biol.*, 141:369-391, 1980).

Researchers have modified antibodies in various ways in order to study their function or to improve their utility as therapeutic agents. In some of the earliest modifications, researchers used double-stranded DNA sequences to express the $V_H$ or $V_L$ domains, but none of the sequence of the constant region (see, e.g., EP-A-0 088 994; Schering Corporation). Other fragments and chimeric antibodies have also been made. One particular type of chimera, commonly referred to as a CDR-grafted antibody, includes sequences from two antibodies that differ in species of origin (e.g., murine CDRs have been used in place of the naturally occurring CDRs in otherwise human antibodies; see, e.g., U.S. Pat. No. 5,225,539). Researchers hoped that such antibodies would be no more foreign to the human body than a fully human antibody, However, the utility of such antibodies has been restricted, at least in some cases, by a reduction in the antibody's affinity for the antigen. In an attempt to improve affinity, some of the amino acids in the FRs of CDR-grafted antibodies have been changed from those of the acceptor molecule (e.g., a human antibody) to those of the antibody that donated the CDRs (e.g., those of a murine antibody; see, e.g., U.S. Pat. No. 5,585,089; U.S. Pat. No. 5,693,761; U.S. Pat. No. 5,693,762; and U.S. Pat. No. 6,180,370). However, such modifications often result in molecules with increased immunogenicity. There remains a need for antibodies and other binding molecules that do not provoke a strong immune response yet bind strongly to antigen and methods for making such binding molecules.

SUMMARY OF THE INVENTION

The present invention is based, at least in part, on the discovery that strategic modifications of non-human donor antibody amino acids (eg. CDR residue(s) and/or adjacent FR residues) can be used to humanize antibodies. Such modifications modulate the 3D structural fit between donor antibody CDRs and human acceptor antibody framework regions that comprise the variable domains of a CDR-grafted antibody. Whereas prior art methods of humanization have relied on making framework substitutions (in which selected human framework residues are backmutated to the corresponding amino acid residue present in the non-human donor antibody), the instant invention is based, at least in part, on a novel method of humanizing antibodies in which selected variable region residues (e.g. CDR residues and, optionally, adjacent FR residues) are changed in order to accommodate differences in FR amino acid sequences between donor and acceptor antibodies. By focusing on making changes to the CDR region of an immunoglobulin variable region rather than the FR region, an immune response by a subject to a polypeptide comprising such variable regions can be minimized. In one embodiment, such modifications result in humanized antibodies that comprise fully human FR regions and have reduced immunogenicity compared to unmodified CDR.

In one aspect, the invention pertains to a method of humanizing an immunoglobulin (Ig) variable region which comprises a) variable region framework (FR) amino acid residues from an acceptor Ig variable region having acceptor variable region CDR and FR amino acid residues and b) complementarity determining regions (CDRs) from a non-human donor Ig variable region having donor variable region CDR and FR amino acid residues, the method comprising, i) providing data which allows prediction of the conformation of at least one CDR; ii) identifying which FR amino acid residues are predicted to affect the 3-D conformation of the at least one CDR; iii) identifying at least one candidate donor CDR amino acid residue for substitution with an elected amino acid residue, wherein the elected amino acid residue conformationally accommodates an amino acid residue difference between the donor and acceptor in the FR without affecting the CDR conformation; and iv) substituting the at least one candidate donor CDR amino acid residue with the elected amino acid residue to form a humanized Ig variable region.

In one embodiment, step (iii) further comprises identifying at least one candidate acceptor FR amino acid residue for substitution with a second elected amino acid residue, wherein the second elected amino acid residue conformationally accommodates a FR amino acid residue difference between the donor Ig variable region and the acceptor Ig variable region without affecting the CDR conformation. In another embodiment, step (iv) further comprises substituting the at least one candidate acceptor FR residue with the second elected amino acid residue.

In one embodiment, step (i) comprises evaluating a 3-dimensional (3D) structure of the non-human donor Ig variable region.

In another embodiment, step (i) comprises evaluating x-ray diffraction data of the non-human donor Ig variable region.

In another embodiment, step (i) comprises evaluating a computer generated model of the non-human donor Ig variable region.

In certain embodiments, the acceptor Ig variable region is derived from a human antibody. In one embodiment, the acceptor Ig variable region is derived from a human consensus sequence. In another embodiment, the acceptor Ig variable region is derived from a human germline sequence.

In another aspect, the invention pertains to a method of designing a humanized Ig variable region which comprises a) variable framework regions (FRs) from an acceptor Ig variable region and b) complementarity determining regions (CDRs) from a non-human donor Ig variable region, the method comprising, (a) identifying framework region (FR) amino acids which differ between the acceptor Ig variable region and the donor Ig variable region;

(b) identifying amino acids adjacent to the FR amino acid(s) identified in step (a);

(c) identifying at least one candidate amino acid from the amino acids identified in step (b) for substitution with an elected amino acid residue which conformationally accommodates the FR amino acid(s) identified in step (a).

In certain embodiments, the method further comprises substituting the elected amino acid residue at the candidate amino acid position.

In one embodiment, the FR amino acid identified in step (a) is a canonical FR residue. In another embodiment, the amino acid identified in step (b) is immediately adjacent to the FR amino acid identified in step (a). In another embodiment, the amino acid identified in step (b) is within about 4 Å of 3-D space from the FR amino acid identified in step (a).

In one embodiment, the elected amino acid residue is identified by side chain repacking. In another embodiment, the elected amino acid residue is selected from all possible rotamers of all possible amino acids. In another embodiment, the elected amino acid residue is selected from a subset of all possible rotamers of all possible amino acids.

In another embodiment, the elected amino acid residue is identified as an amino acid that is most commonly present at the position of the candidate amino acid within a set of homologous antibody variable region sequences having the same FR amino acid as the FR amino acid identified in step (a).

In another embodiment, the elected amino acid residue is selected from a subset of all possible rotamers of all possible amino acids wherein the subset comprises all possible rotamers of amino acids that are commonly present at the position of the candidate amino acid within a set of homologous antibody variable region sequences having the same FR amino acid as the FR amino identified in step (a).

In another aspect, the invention pertains to a method of designing a humanized Ig variable region, the method comprising, a) selecting a non-human donor Ig variable region comprising donor variable region CDR and FR amino acid residues; b) selecting an acceptor Ig variable region comprising acceptor variable region CDR and FR amino acid residues c) identifying at least one candidate amino acid residue in at least one CDR of the donor Ig variable region for substitution with an elected amino acid residue, where: (i) the candidate amino acid is immediately adjacent to an amino acid of the acceptor FR region; or (ii) the candidate amino acid is predicted to have a side chain atom whose Van der Waals surface is within about 4 Å of an acceptor variable region FR amino acid residue in a 3D immunoglobulin model and is predicted to interact with at least one variable region FR amino acid residue of the humanized Ig chain.

In one embodiment, the method further comprises identifying at least one candidate FR amino acid residue in the acceptor Ig variable region for substitution with a second elected amino acid residue, wherein:

(i) the candidate FR amino acid residue is immediately adjacent to a CDR amino acid residue of the donor Ig variable region; or (ii) the candidate FR amino acid residue is predicted to have a side chain atom whose Van der Waals surface is within about 4 Å of a CDR amino acid residue of the donor Ig variable region in a 3D immunoglobulin model and is predicted to interact with at least one variable region CDR amino acid residue of the humanized Ig chain.

In one embodiment, the method further comprises substituting the elected amino acid residue(s) at the candidate amino acid residue position. In another embodiment, the method further comprises substituting the second elected amino acid residue(s) at the candidate FR amino acid residue position.

In another embodiment, the Ig variable region is present in an intact antibody molecule. In another embodiment, the Ig variable region is present in a fragment of an antibody molecule.

In one embodiment, the Ig variable region is present in a molecule selected from the group consisting of: an antibody, an antibody light chain (VL), an antibody heavy chain (VH), a single chain antibody (scFv), a F(ab')$_2$ fragment, a Fab fragment, an Fd fragment, and a single domain fragment.

In another embodiment, the Ig variable region is a light chain variable region. In another embodiment, the Ig chain is a heavy chain variable region.

In yet another embodiment, the humanized Ig chain comprises at least one variable region FR amino acid substitution.

In one embodiment, the elected amino acid is from a subset of amino acids having characteristic side chain chemistry, said subset of amino acids selected from the group consisting of: uncharged polar amino acid residues, nonpolar amino acid residues, positively charged amino acid residues, and negatively charged amino acid residues.

In one embodiment, the method is repeated at least one time. In another embodiment, in the method is conducted in silico.

In one embodiment, the method further comprises expressing a polypeptide comprising the humanized Ig variable region.

In one embodiment, the polypeptide is expressed in an expression system selected from the group consisting of: an acellular extract expression system, a phage display expression system, a prokaryotic cell expression system, and a eukaryotic cell expression system.

In one embodiment, the non-human donor antibody is a mouse antibody. In another embodiment, the non-human donor antibody is a primate antibody.

In one embodiment, the invention pertains to a nucleic acid molecule comprising a nucleotide sequence which encodes for a polypeptide comprising the humanized variable region made by the method of the invention.

In another embodiment, the invention pertains to a host cell comprising a nucleic acid molecule of the invention.

In yet another embodiment, the invention pertains to a polypeptide comprising the humanized Ig variable region produced by the method of the invention.

In one embodiment, the invention pertains to a pharmaceutical composition comprising the polypeptide of the invention.

In another embodiment, the invention also pertains to a method for treating or preventing a human disorder or disease comprising, administering a therapeutically-effective amount of the pharmaceutical composition of the invention, such that therapy or prevention of the human disease or disorder is achieved.

In yet another embodiment, the invention pertains to an antibody, or binding fragment thereof, produced by culturing the host cell of the invention under conditions such that antibody, or binding fragment thereof, is expressed.

In one embodiment, at least one donor antibody CDR is a CDR of an antibody selected from the group consisting of: an anti-Cripto antibody, an anti-CD40L antibody, an anti-VLA4 antibody, and an anti-MCP antibody.

In another aspect, the invention pertains to a humanized Ig light chain variable region comprising the amino acid sequence selected from the group consisting of SEQ ID NOs: 6-13.

In yet another aspect, the invention pertains to a humanized Ig light chain variable region comprising the amino acid sequence selected from the group consisting of SEQ ID NOs: 8, 9, and 11.

In still another aspect, the invention pertains to a humanized Ig heavy chain variable region comprising an amino acid sequence selected from the group consisting of SEQ ID NO:22, SEQ ID NO:23, SEQ ID NO:24, and SEQ ID NO:25.

In one embodiment, the invention pertains to an antibody or fragment thereof comprising a humanized Ig sequence of the invention.

In another embodiment, the invention pertains to a humanized Ig light chain variable region comprising the amino acid sequence shown in SEQ ID NO: 11.

In still another aspect, the invention pertains to a humanized Ig heavy chain comprising the amino acid sequence SEQ ID NO: 17.

In another aspect, the invention pertains to a humanized Ig heavy chain comprising the amino acid sequence SEQ ID NO: 18.

In yet another aspect, the invention pertains to a murine antibody or antigen-binding fragment thereof comprising the Ig heavy chain variable region set forth as SEQ ID NO:19.

In one embodiment, the invention pertains to a method for treating or preventing a human disorder or disease comprising, administering a therapeutically-effective amount of the pharmaceutical composition of the invention, such that therapy or prevention of the human disease or disorder is achieved. In one embodiment, the disorder or disease is neoplasia. In another embodiment, the disease or disorder is an inflammatory disease or disorder.

The details of one or more embodiments of the invention are set forth in the accompanying drawings and the description below. Other features, objects, and advantages of the invention will be apparent from the description and drawings, and from the claims. The contents of any patents, patent applications, and other references cited in the specification are hereby incorporated by reference in their entirety.

BRIEF DESCRIPTION OF THE DRAWINGS

FIG. 1 shows an alignment of the light chains of donor murine B3F6, the acceptor, and the various humanized forms made. The variable light chain of murine B3F6 is shown in SEQ ID NO:3, of BAC01733 is shown in SEQ ID NO:4, and of murine B3F6 CDRs grafted into the human acceptor is shown in SEQ ID NO:5. The versions of humanized B3F6 humanized according to the methods of the invention are shown in SEQ ID Nos:6-13. FR amino acid residues found only in the donor sequence bolded and italicized while canonical CDR-interacting residues are indicated in bold. The positions of CDR residues selected for mutation are indicated by an asterisk. Kabat numbers are indicated along the top of the alignment.

FIG. 4 shows an alignment of the heavy chain variable regions (VH) of donor murine HP1/2, the germline acceptor (huIGHV1-f), and the various humanized forms made. The variable heavy chain of murine HP/2 is shown in SEQ ID NO:19, of huIGHV1-f is shown in SEQ ID NO:20, and of murine HP1/2 CDRs grafted into the human acceptor is shown in SEQ ID NO:21. The versions of HP 1/2 heavy chain humanized according to the methods of the invention are shown in SEQ ID Nos:22-25. Canonical amino acid residues found within the donor and acceptor sequences are underlined and italicized. The positions of the CDRs are indicated by the shaded area, while the position of residues selected for mutation are indicated as underlined and bold. Kabat numbers are indicated along the top of the alignment.

FIG. 5 shows an alignment of the light chain variable regions (VLs) of donor murine HP1/2, the germline acceptor (B3), and the CDR graft is shown in FIG. 2. The variable light chain of murine HP1/2 is shown in SEQ ID NO:26, of B3 is shown in SEQ ID NO:27, and of the murine HP1/2 CDRs grafted into the human acceptor is shown in SEQ ID NO:28. Annotation is the same as in FIG. 4.

DETAILED DESCRIPTION OF THE INVENTION

Figure 2:
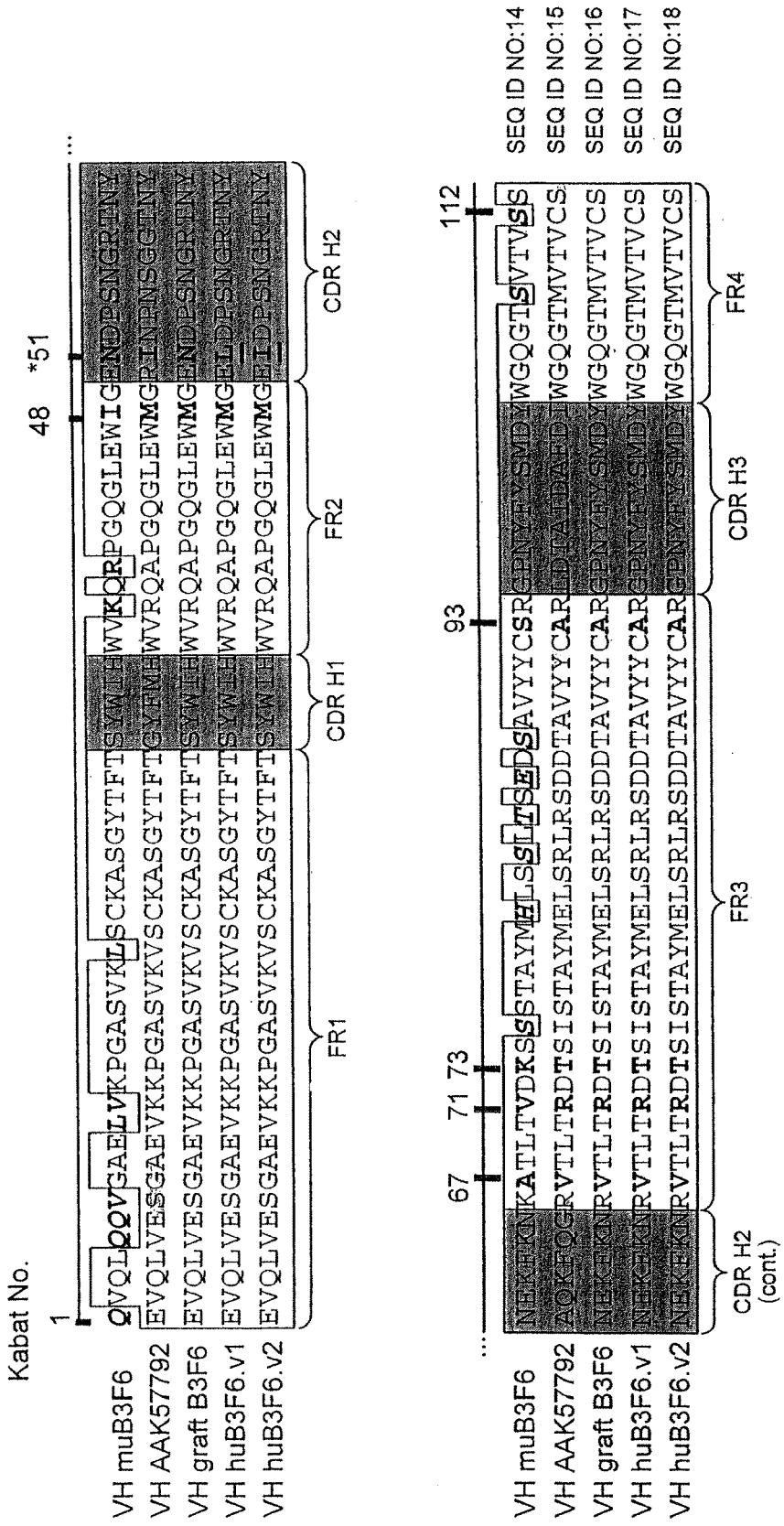
FIG. 2 shows an alignment of the heavy chains of donor murine B3F6, the acceptor, and the various humanized forms made is shown in FIG. 2. The variable heavy chain of murine B3F6 is shown in SEQ ID NO:14, of AAK57792 is shown in SEQ ID NO:15, and of murine B3F6 CDRs grafted into the human acceptor is shown in SEQ ID NO:16. The versions of humanized B3F6 humanized according to the methods of the invention are shown in SEQ ID Nos:17 and 18. Annotation is the same as in FIG. 1.
Figure 3:
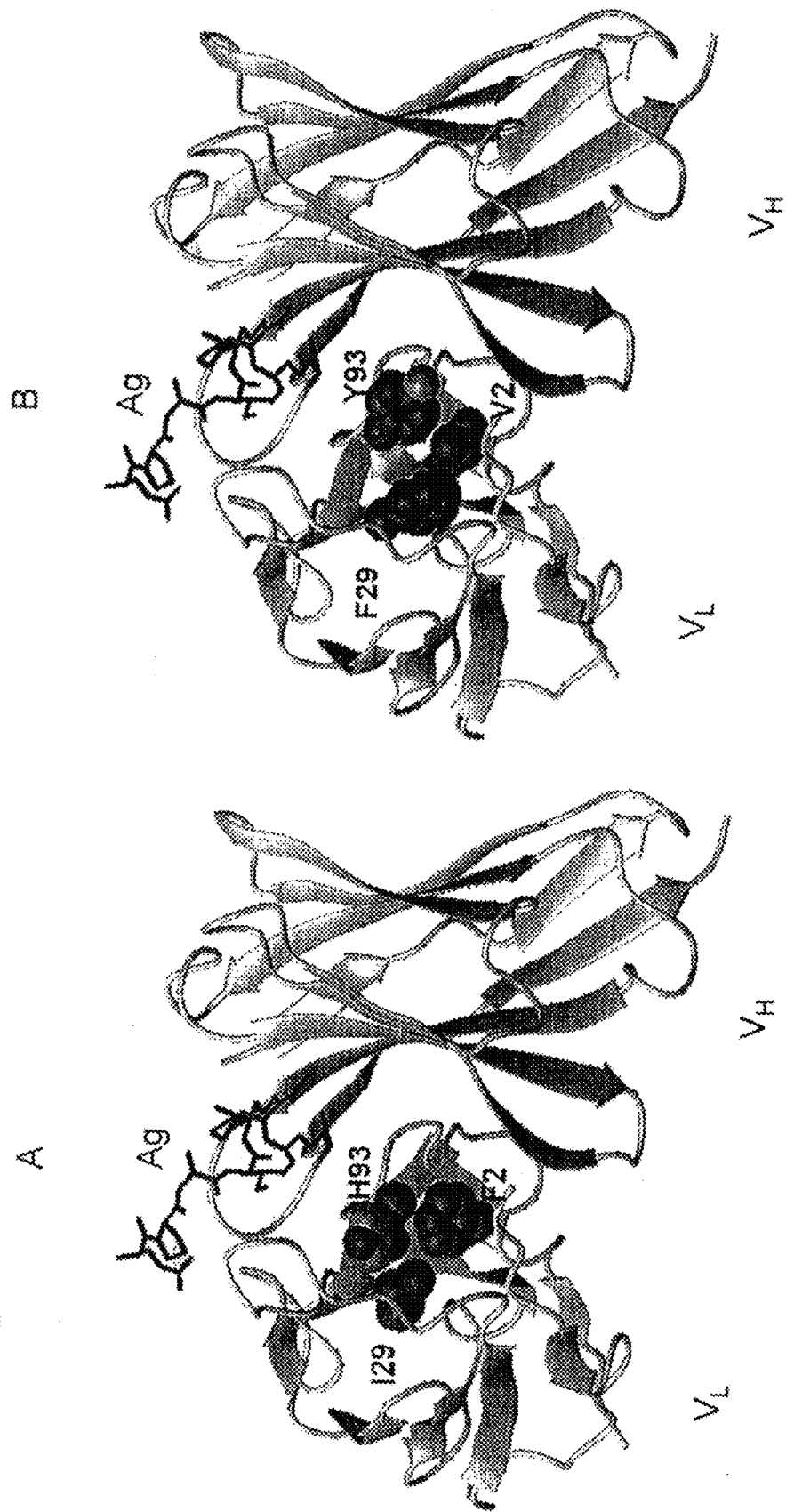
FIG. 3 panel A shows a three dimensional representation of light and heavy chains of a B3F6 antibody molecule after traditional humanization. Traditional humanization methods require backmutation of the human residue V at amino acid position 2 of VL of the human framework to the murine residue F to support the conformations of the murine CDR residues I29 and H98. Panel B shows the same light and heavy chain after alternative humanization using the methods described herein. These methods allow retention of the human amino acid V at position 2 of the VL of the human framework while mutations at positions 29 (I to F) and 98 (H to Y) are introduced into the CDRs to preserve CDR conformation.

The present invention is based on the discovery of novel methods for humanization of immunoglobulin variable regions. As set forth herein, strategic modifications of donor antibody variable region amino acid residues (e.g., CDR amino acid residue(s) and/or framework amino acid residues) can be used to modulate the 3D structural fit between donor antibody CDR and acceptor antibody framework domains that comprise the variable domains of a CDR-grafted antibody. The effect of such modifications is to obtain a humanized antibody with low immunogenicity. The invention also pertains to antigen binding molecules made using these novel methods and methods of their use.

Various aspects of the invention are described in further detail in the following subsections:

I. DEFINITIONS

As used herein, the term "immunoglobulin" or "Ig" refers to a protein consisting of one or more polypeptides encoded by or substantially encoded by immunoglobulin genes. The recognized immunoglobulin genes include the kappa, lambda, alpha, gamma, delta, epsilon and mu constant region genes, as well as the myriad immunoglobulin variable region genes. The immunoglobulins may exist in a variety of forms besides antibodies; including, for example, Fv, Fab and (Fab')$_2$, as well as bifunctional hybrid antibodies (e.g.; Lanzavecchia et al., *Eur. J. Immunol.* 17, 105 (1987)) and in single chains (e.g., Huston, et al., *Proc. Nat. Acad. Sci. U.S.A.,* 85, 5879-5883 (1988) and Bird, et al., *Science,* 242, 423-426 (1988), which are incorporated herein by reference). (See, generally, Hood, et al., "Immunology", Benjamin, N.Y., 2$^{nd}$ ed. (1984), and Hunkapiller and Hood, *Nature,* 323, 15-16 (1986), which are incorporated herein by reference). As used herein, the term "immunoglobulin (Ig) chain" includes at least an "Ig variable region" which comprises the FR and CDRs and are the amino terminal portion of an Ig chain which confers antigen binding to the molecule and, optionally, one or more "constant regions" which control effector function of the chain or antibody comprising the chain. In one embodiment, a light chain includes $V_L$ and $C_L$ domains, and an Ig heavy chain includes $V_H$, $C_H1$, $C_H2$, and $C_H3$ domains.

"Humanized" forms of non-human (e.g., murine) immunoglobulin variable regions are variable regions which comprise an amino acid sequence of a non-human antibody which is modified (by changing the amino acid sequence) to become more "human-like." Preferably, such antibodies contain minimal sequence derived from non-human immunoglobulin. The constant regions of non-human donor light and heavy chains are usually replaced by constant regions from an acceptor antibody. Using the methods described herein, residues from a hyper-variable region of the acceptor antibody are replaced by residues from a hypervariable region of a non-human donor antibody (e.g., derived from a mammal such as a mouse, rat, rabbit, hamster, or nonhuman primate) having the desired specificity and/or affinity. Appropriate CDR amino acid residues may then be modified using rational design as described herein to optimize binding to antigen. In some instances, a binding molecule of the invention comprises fully human framework regions. In other embodiment, Fv framework region (FR) residues of the human immunoglobulin may also be replaced by corresponding non-human residues or, in a preferred embodiment, FR residues may be modified using the rational design methods described herein. Preferably, any such framework residues that are substituted (e.g., backmutated to the non-human donor residue) are not close to the CDRs and/or do not affect CDR conformation. Furthermore, humanized antibodies may comprise residues which are not found in the recipient antibody or in the donor antibody. These modifications may be made to further refine antibody performance or expression.

As used herein the term "variable region CDR amino acid residues" includes amino acids in a CDR or complementarity determining region as identified using sequence or structure based methods. As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth below in Table 1 as a comparison. Preferably, the term "CDR" is a CDR as defined by Kabat based on sequence comparisons.

TABLE 1

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein the term "variable region framework (FR) amino acid residues" or "framework residues" refers to those amino acids in the framework region of an Ig chain. The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but is intended to reference only those amino acids outside of the CDRs. For the specific example of a heavy chain variable region and for the CDRs as defined by Kabat et al., framework region 1 corresponds to the domain of the variable region encompassing amino acids 1-30; region 2 corresponds to the domain of the variable region encompassing amino acids 36-49; region 3 corresponds to the domain of the variable region encompassing amino acids 66-94, and region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above.

As used herein, the term "data which allows identification of amino acid sequence differences between the donor and acceptor variable region FR amino acid residues" includes data, e.g., generated based on examination of Ig structure or sequence comparison, that informs one of ordinary skill in the art of amino acid residues in the donor antibody that differ from corresponding amino acid residues in the acceptor antibody.

As used herein, the term "amino acid residues predicted to affect the 3-D conformation of the CDRs" includes those amino acid residues in the FR that are likely to affect the structure of the Ig chain backbone to thereby affect CDR 3D structure and/or those amino acids which affect the positions of one or more CDR amino acid side chains necessary for antigen binding.

As used herein, the term "conformationally accommodates" includes amino acids which allow for the fit of other amino acids (e.g. those amino acids which are sterically complementary, electrostatically complementary, hydrogen bond donor-acceptor complementary, or otherwise complementary) such that the 3D conformation of CDRs, e.g., as determined by preserved antigen binding or by actual observation or modeling of CDR conformation, is preserved. As used herein the term "CDR conformation" refers to the 3D structure of a CDR, e.g. the positioning of antigen contacting residues of a CDR loop.

As used herein, the term "donor" or "donor Ig variable region sequence" is intended to mean an Ig variable region amino acid sequence from which CDRs of a humanized Ig variable region are derived. In general, a donor Ig variable region sequence will be derived from an antibody molecule. The donor CDRs confer binding specificity of a donor molecule to an acceptor molecule. It should be under-stood that a donor Ig region does not have to be from a different species than an acceptor antibody. Instead, it is sufficient that the donor is a separate and distinct molecule. In a preferred embodiment, a donor antibody is a non-human antibody.

As used herein, the term "acceptor" or "acceptor Ig variable region sequence" is intended to mean an Ig variable region amino acid sequence into which donor CDRs are to be placed. In one embodiment, an acceptor antibody is a human antibody. However, acceptor Ig variable region sequences do not have to be derived from antibody sequences that exist in nature. In another embodiment, an acceptor Ig variable region sequence is derived from human germline sequences. In another embodiment, an acceptor Ig variable region sequence may be a consensus sequence based on the most commonly occurring amino acid residue at any position when multiple human sequences are aligned. In yet another embodiment an acceptor Ig variable region sequence may be derived from a human antibody (or germline or consensus sequence) but may comprise one or more FR amino acid modifications which optimize antibody performance and/or expression. Preferably, and such FR amino acid modifications are not close to CDRs and/or are made to amino acids that do not affect CDR conformation.

As used herein, the term "adjacent to an amino acid of the acceptor FR region" includes variable region amino acids (e.g. CDR and/or FR amino acids) which are near (e.g. within 25 Angstroms or less, preferably 15 Angstroms or less) an amino acid of the acceptor FR region as determined by an evaluation of the structure (e.g. primary, secondary, or tertiary structure) of the variable region polypeptide. In certain embodiments, an amino acid is adjacent to an amino acid of the acceptor FR region if it is present at an amino acid position that is within 5 or fewer amino acid positions of an acceptor FR amino acid in a variable region sequence (e.g. within 4, 3, 2, or 1 amino acid position). In other embodiments, an amino acid is adjacent to an amino acid of the acceptor FR region if it has an atom that is within 25 Angstroms of 3-D space (e.g. within 20, preferably 15, more preferably 10, or particular preferably 5 Angstroms of 3-D space, in particular within 4 Angstroms of 3-D space) from an atom of an amino acid of the acceptor FR region as determined by an evaluation of a 3-dimensional structure of the variable region.

As used herein, the term "immediately adjacent to an amino acid of the acceptor FR region" includes variable region amino acids (e.g. CDR amino acids, and optionally FR amino acids) which are directly next to (i.e., which form covalent bonds with) FR amino acids in chain of amino acids in a variable region sequence.

As used herein, the term "side chain atom whose Van der Waals surface is within about 4 Å of an acceptor variable region FR amino acid residue" includes those amino acids which, when their Van der Waals surface is projected, come within about 4 Å of an acceptor variable region FR amino acid residue. Van der Waals forces or surfaces for a given atom can be predicted or can be measured using techniques known in the art.

As used herein, the term "predicted to interact with at least one variable region FR amino acid residue of the humanized Ig chain" includes those amino acids which would be predicted, based on techniques known to those of skill in the art, to interact (e.g., via electrostatic interaction, Van der Waals forces, or hydrophobic interaction) with at least one variable region FR amino acid residue of the humanized Ig chain.

As used herein, the term "3D structure" refers to the known, predicted and/or modeled position(s) in three-dimensional space that are occupied by the atoms or amino acids, e.g., of an Ig variable region. A number of methods for identifying or predicting 3D structure at the molecular/atomic level are known in the art, including X-ray crystallography, NMR, structural modeling, and a variety of predominately in silico approaches to structural prediction/determination. Such approaches can incorporate, e.g., factors such as the extent of homology of the (macro)molecule or portion thereof of interest with known and/or predicted 3D structures of other (macro)molecules, knowledge of primary and/or secondary structural features present in the (macro)molecule of interest, modeling of hydrogen bonding, van der Waals forces, hydrophobic interactions, etc., to generate at least one 3D structural model for the (macro)molecule or portions thereof of interest. Additionally, knowledge of antibody framework domain amino acid residue positions generally important for CDR conformation in antibodies of related sequence constitutes 3D structural information for purposes of the present invention.

As used herein, the term "in silico" includes information regarding molecules (e.g., humanized variable regions or polypeptides comprising such humanized variable regions) created in a computer memory, i.e., on a silicon or other like chip. Stated otherwise, in silico means "virtual."

As used herein, the term "neoplasia" includes uncontrolled cell growth, including either benign or malignant tumors. As used herein, the term "malignancy" refers to a non-benign tumor or a cancer.

As used herein, the term "cancer" includes a malignancy characterized by deregulated or uncontrolled cell growth, for instance carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor). A subject having "cancer", for example, may have a tumor or a white blood cell proliferation such as leukemia. In certain embodiments, a subject having cancer is a subject having a tumor, such as a solid tumor. Cancers involving a solid tumor include but are not limited to non small cell lung cancer (NSCLC), testicular cancer, lung cancer, ovarian cancer, uterine cancer, cervical cancer, pancreatic cancer, colorectal cancer (CRC), breast cancer, as well as on prostate, gastric, skin, stomach, esophagus and bladder cancer.

The term "binding affinity", as used herein, includes the strength of a binding interaction and therefore includes both the actual binding affinity as well as the apparent binding affinity. The actual binding affinity is a ratio of the association rate over the disassociation rate. Therefore, conferring or optimizing binding affinity includes altering either or both of these components to achieve the desired level of binding affinity. The apparent affinity can include, for example, the avidity of the interaction. For example, a bivalent altered variable region binding fragment can exhibit altered or optimized binding affinity due to its valency. Binding affinities may also be modeled, with such modeling contributing to selection of residue alterations in the methods of the current invention.

The term "antibody", as used herein, includes monoclonal antibodies (including full length monoclonal antibodies), polyclonal antibodies, multispecific antibodies (e.g., bispecific antibodies), chimeric antibodies, CDR-grafted antibodies, humanized antibodies, or human antibodies.

As used herein, the term "fragment" of an antibody molecule includes antigen-binding fragments of antibodies, for example, an antibody light chain ($V_L$), an antibody heavy chain ($V_H$), a single chain antibody (scFv), a $F(ab')_2$ fragment, a Fab fragment, an Fd fragment, an Fv fragment, and a single domain antibody fragment (DAb).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described, e.g., in Clack-son et al., Nature 352: 624-628 (1991) and Marks et al., J. Mol. Biol. 222:581-597 (1991).

The term "chimeric immunoglobulin" or antibody refers to an immunoglobulin or antibody comprising amino acid sequences derived from different species. Chimeric immunoglobulins or antibodies can be constructed, for example by genetic engineering, from immunoglobulin gene segments belonging to different species.

The phrase "candidate amino acid residue position", as used herein, includes an amino acid position identified within the CDR or FR domain of an antibody of the present invention, wherein the substitution of the candidate amino acid is modeled, predicted, or known to impact the structural fit between CDR domains and FR domains of an antibody upon alteration, deletion, insertion, or substitution with another amino acid.

The term "elected amino acid", as used herein, refers to an amino acid residue(s) that has been selected by the methods of the present invention for substitution into a candidate amino acid residue position within the antibody. Substitution of the candidate amino acid residue position with the elected amino acid residue enhances or the structural fit between donor CDR domains and acceptor FR domains of an Ig variable region.

The terms "amino acid alteration" or "alteration for said amino acid," as used herein, include a change in the amino acid sequence of a predetermined amino acid sequence. Exemplary alterations include insertions, substitutions, and deletions. The term "amino acid substitution", as used herein, includes the replacement of an existing amino acid residue side chain chemistry in a predetermined amino acid sequence with another, different amino acid residue (e.g., having different side chain chemistry).

The term "naturally occurring amino acid residue," as used herein, includes one encoded by the genetic code, generally selected from the group consisting of: alanine (Ala); arginine (Arg); asparagine (Asn); aspartic acid (Asp); cysteine (Cys); glutamine (GM); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val).

The term "non-naturally occurring amino acid residue" as used herein, includes an amino acid residue other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA.

The term "treatment" refers to both therapeutic treatment and prophylactic or preventative measures. Those in need of treatment include those already with the disorder as well as those in which the disorder is to be prevented.

The term "disorder or disease" is any condition that would benefit from treatment with the antibody variant. This includes chronic and acute disorders or diseases including those pathological conditions which predispose the mammal to the disorder in question.

The terms "cell", "cell line", "cell culture", or "host cell", as used herein, includes "transformants", "transformed cells", or "transfected cells" and progeny thereof. Host cells within the scope of the invention include prokaryotic cells such as E. coli, lower eukaryotic cells such as yeast cells, insect cells, and higher eukaryotic cells such as vertebrate cells, for example, mammalian cells, e.g., Chinese hamster ovary cells and NSO myeloma cells.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from nucleic acid molecules as they exist in natural cells. However, an isolated nucleic acid molecule can include a nucleic acid molecule contained in cells that ordinarily express the nucleic acid molecule where, for example, the nucleic acid molecule is in a chromosomal location different from that in which it is found in natural cells.

II. IMMUNOGLOBULIN VARIABLE REGIONS FOR HUMANIZATION

The methods of the invention can be performed on immunoglobulin variable regions, whether present in isolated form or in Ig chains, antibodies, modified forms of antibodies, or antigen binding fragments thereof. The subject immunoglobulin variable regions for humanization are chimeric in that they comprise CDR sequences derived from donor antibodies and FR sequences derived from acceptor antibodies. It will be understood that the chimeric molecules for humanization need not be synthesized in order to practice the methods of the invention. For example in one embodiment, donor and acceptor Ig variable regions can be identified, candidate donor CDR residues for modification can be selected, e.g., based on 3D modeling or database selection, and the humanized form of the molecule can optionally be synthesized without having produced the donor, acceptor, or starting chimeric antibody.

Methods for making/selecting donor and acceptor Ig variable regions sequences are described in further detail below.

A. Donor Ig Variable Region Sequences

Donor Ig variable region sequences may be derived from antibodies known in the art or antibodies which can be made using any of a number of art recognized protocols. For example, donor antibodies can be raised in mammals (e.g., non-human mammals) by multiple subcutaneous or intraperitoneal injections of a relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes.

Donor antibodies may be produced in a non-human mammal, e.g., murine, guinea pig, primate, hamster, rabbit or rat, by immunizing the animal with the antigen or a fragment thereof. See Harlow & Lane, supra, incorporated by reference for all purposes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). The donor antibodies can be of the IgA, IgD, IgE, IgG, or IgM class.

Rabbits or guinea pigs are typically used for making polyclonal antibodies, whereas mice are typically used for making monoclonal antibodies. Monoclonal antibodies can be prepared against a fragment by injecting an antigen fragment into a mouse, preparing "hybridomas" and screening the hybridomas for an antibody that specifically binds to the antigen. In this well known process (Kohler et al., (1975), *Nature,* 256: 495) the relatively short-lived, or mortal, lymphocytes from the mouse which has been injected with the antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. Hybridomas produce antibodies which are homogeneous against a desired antigen and, in reference to their pure genetic parentage, are termed "monoclonal." As used herein, the term monoclonal refers to antibodies which are homogeneous against a desired antigen regardless of the method by which they were made.

Methods for producing monoclonal antibodies have been known for some time (see, e.g., Kohler and Milstein, *Nature* 256:495-497, 1975), as have techniques for stably introducing immunoglobulin-encoding DNA into myeloma cells (see, e.g., Oi et al., *Proc. Natl. Acad. Sci. USA* 80:6351-6355, 1983). These techniques, which include in vitro mutagenesis and DNA transfection, allow the construction of recombinant immunoglobulins and can be used to produce the polypeptide used in the methods of the invention or those that result therefrom (e.g., therapeutic and diagnostic antibodies). Production methods, vectors, and hosts are described further below.

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Optionally, antibodies may be screened for binding to a specific region or desired fragment of the antigen without binding to other nonoverlapping fragments of the antigen. The latter screening can be accomplished by determining binding of an antibody to a collection of deletion mutants of the antigen and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay in which a test and reference antibody compete for binding to the antigen. If the test and reference antibodies compete, then they bind to the same epitope or epitopes sufficiently proximal such that binding of one antibody interferes with binding of the other.

In another embodiment, DNA encoding the desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments (e.g., antigen binding sites) may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. *Immunol. Today* 21:371; Nagy et al. 2002. *Nat. Med.* 8:801; Huie et al. 2001. *Proc. Natl. Acad. Sci. USA* 98:2682; Lui et al. 2002. *J. Mol. Biol.* 315:1063, each of which is incorporated herein by reference. Several publications (e.g., Marks et al. *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. *Nat. Biotechnol.* 18:1287; Wilson et al. 2001. *Proc. Natl. Acad. Sci. USA* 98:3750; or Irving et al. 2001 *J. Immunol. Methods* 248:31. In yet another embodiment, cell surface libraries can be screened for antibodies (Boder et al. 2000. Proc. Natl. Acad. Sci. USA 97:10701; Daugherty et al. 2000 *J. Immunol. Methods* 243:211. Such procedures provide alternatives to traditional hybridoma techniques for the isolation and subsequent cloning of monoclonal antibodies.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the polypeptides of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered to provide obtain polypeptides of the present invention.

Variable and constant domains can be separately cloned, e.g., using the polymerase chain reaction and primers which are selected to amplify the domain of interest. In addition, the sequences of many antibody variable and constant domains are known and such domains can be synthesized using methods well known in the art. For example, constant region domains can be selected having a particular effector function (or lacking a particular effector function) or with a particular modification to reduce immunogenicity. Alternatively, variable domains can be obtained from libraries of variable gene sequences from an animal of choice. Libraries expressing random combinations of domains, e.g., $V_H$ and $V_L$ domains, can be screened with a desired antigen to identify elements which have desired binding characteristics. Methods of such screening are well known in the art. For example, antibody gene repertoires can be cloned into a λ bacteriophage expression vector (Huse, W D et al. (1989). *Science,* 2476:1275). In addition, cells (Francisco et al. (1994), *PNAS,* 90:10444; Georgiou et al. (1997), *Nat. Biotech.*, 15:29; Boder and Wittrup (1997) *Nat. Biotechnol.* 15:553; Boder et al. (2000), *PNAS,* 97:10701; Daugtherty, P. et al. (2000) *J. Immunol. Methods.* 243:211) or viruses (e.g., Hoogenboom, H R. (1998), *Immunotechnology* 4:1; Winter et al. (1994). *Annu. Rev. Immunol.* 12:433; Griffiths, A D. (1998). *Curr. Opin. Biotechnol.* 9:102) expressing antibodies on their surface can be screened. Those skilled in the art will also appreciate that DNA encoding antibody domains may also be derived from antibody phage libraries, e.g., using pd phage or Fd phagemid technology. Exemplary methods are set forth, for example, in EP 368 684 B1; U.S. Pat. No. 5,969,108; Hoogenboom et al., (2000) *Immunol. Today* 21:371; Nagy et al. (2002) *Nat. Med.* 8:801; Huie et al. (2001), *PNAS,* 98:2682; Lui et al. (2002), *J. Mol. Biol.* 315:1063, each of which is incorporated herein by reference. Several publications (e.g., Marks et al. (1992), *Bio/Technology* 10:779-783) have described the production of high affinity antibodies by chain shuffling, as well as combinatorial infection and in vivo recombination as a strategy for constructing large phage libraries. In another embodiment, ribosomal display can be used to replace bacteriophage as the display platform (see, e.g., Hanes, et al. (1998), *PNAS* 95:14130; Hanes and Pluckthun. (1999), *Curr. Top. Microbiol. Immunol.* 243:107; He and Taussig. (1997), *Nuc. Acids*

*Res.*, 25:5132; Hanes et al. (2000), *Nat. Biotechnol.* 18:1287; Wilson et al. (2001), *PNAS*, 98:3750; or Irving et al. (2001) *J. Immunol. Methods* 248:31).

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis. In many cases immunoreative antibodies for antigens of interest have been reported in the literature.

B. Exemplary Donor Antibody Target Molecules

Typically, donor Ig variable region sequences are selected based on the target antigen to which antibodies comprising the sequences bind. In one embodiment, a donor Ig variable region sequence is selected based on its specificity for an antigen targeted for reduction or elimination, e.g., from a tissue or from the circulation. In one embodiment, a donor Ig variable region sequence is selected based on its specificity for an antigen that can be used to detect the presence of a target molecule (e.g., to detect a contaminant or diagnose a condition or disorder). In yet another embodiment, a donor Ig variable region sequence is selected based on its specificity for a specific cell type in a subject (e.g., a tumor cell or blood clot).

In one embodiment, a donor antibody of the present invention may be immunoreactive with one or more tumor-associated antigens. For example, for treating a cancer or neoplasia an antigen binding domain of a polypeptide preferably binds to a selected tumor associated antigen. Given the number of reported antigens associated with neoplasias, and the number of related antibodies, those skilled in the art will appreciate that a polypeptide of the invention may be derived from any one of a number of whole antibodies. More generally, starting antibodies useful in the present invention may be obtained or derived from any antibody (including those previously reported in the literature) that reacts with an antigen or marker associated with the selected condition. Further, a donor antibody, or fragment thereof, used to generate the disclosed binding molecules may be murine, human, chimeric, humanized, non-human primate or primatized. Exemplary tumor-associated antigens bound by the donor antibodies used in the invention include for example, pan B antigens (e.g. CD20 found on the surface of both malignant and non-malignant B cells such as those in non-Hodgkin's lymphoma) and pan T cell antigens (e.g. CD2, CD3, CD5, CD6, CD7). Other exemplary tumor associated antigens comprise but are not limited to MAGE-1, MAGE-3, MUC-1, HPV 16, HPV E6 & E7, TAG-72, CEA, α-Lewis$^y$, L6-Antigen, CD19, CD22, CD25, CD30, CD33, CD37, CD44, CD52, CD56, mesothelin, PSMA, HLA-DR, EGF Receptor, VEGF Receptor, and HER2Receptor.

Previously reported antibodies that react with tumor-associated antigens may used as donor antibodies. Exemplary antibodies capable of reacting with tumor-associated antigens include: 2B8, Lym 1, Lym 2, LL2, Her2, B1, BR96, MB1, BH3, B4, B72.3, 5E8, B3F6, 5E10, α-CD33, α-CanAg, α-CD56, α-CD44v6, α-Lewis, and α-CD30.

More specifically, exemplary antibodies include, but are not limited to 2B8 and C2B8 (Zevalin® and Rituxan®, IDEC Pharmaceuticals Corp., San Diego), Lym 1 and Lym 2 (Techniclone), LL2 (Immunomedics Corp., New Jersey), Trastuzumab (Herceptin®, Genentech Inc., South San Francisco), Tositumomab (Bexxar®, Coulter Pharm., San Francisco), Alemtzumab (Campath®, Millennium Pharmaceuticals, Cambridge), Gemtuzumab ozogamicin (Mylotarg®, Wyeth-Ayerst, Philadelphia), Cetuximab (Erbitux®, Imclone Systems, New York), Bevacizumab (Avastin®, Genentech Inc., South San Francisco), BR96, BL22, LMB9, LMB2, MB1, BH3, B4, B72.3 (Cytogen Corp.), SS1 (NeoPharm), CC49 (National Cancer Institute), Cantuzumab mertansine (ImmunoGen, Cambridge), MNL 2704 (Milleneum Pharmaceuticals, Cambridge), Bivatuzumab mertansine (Boehringer Ingelheim, Germany), Trastuzumab-DM1 (Genentech, South San Francisco), My9-6-DM1 (ImmunoGen, Cambridge), SGN-10, -15, -25, and -35 (Seattle Genetics, Seattle), and 5E10 (University of Iowa). In preferred embodiments, the starting antibodies of the present invention will bind to the same tumor-associated antigens as the antibodies enumerated immediately above. In particularly preferred embodiments, the polypeptides will be derived from or bind the same antigens as Y2B8, C2B8, CC49 and C5E10.

In a first preferred embodiment, the donor antibody will bind to the same tumor-associated antigen as Rituxan®. Rituxan® (also known as, rituximab, IDEC-C2B8 and C2B8) was the first FDA-approved monoclonal antibody for treatment of human B-cell lymphoma (see U.S. Pat. Nos. 5,843,439; 5,776,456 and 5,736,137 each of which is incorporated herein by reference). Y2B8 (90Y labeled 2B8; Zevalin®; ibritumomab tiuxetan) is the murine starting of C2B8. Rituxan® is a chimeric, anti-CD20 monoclonal antibody which is growth inhibitory and reportedly sensitizes certain lymphoma cell lines for apoptosis by chemotherapeutic agents in vitro. The antibody efficiently binds human complement, has strong FcR binding, and can effectively kill human lymphocytes in vitro via both complement dependent (CDC) and antibody-dependent (ADCC) mechanisms (Reff et al., *Blood* 83: 435-445 (1994)). Those skilled in the art will appreciate that dimeric variants (homodimers or heterodimers) of C2B8 or 2B8, synthetic according to the instant disclosure, may be conjugated with effector moieties according to the methods of the invention, in order to provide modified antibodies with even more effective in treating patients presenting with CD20+ malignancies.

In other preferred embodiments of the present invention, the donor antibody will bind to the same tumor-associated antigen as CC49. CC49 binds human tumor-associated antigen TAG-72 which is associated with the surface of certain tumor cells of human origin, specifically the LS174T tumor cell line. LS174T [American Type Culture Collection (herein ATCC) No. CL 188] is a variant of the LS180 (ATCC No. CL 187) colon adenocarcinoma line.

It will further be appreciated that numerous murine monoclonal antibodies have been developed which have binding specificity for TAG-72. One of these monoclonal antibodies, designated B72.3, is a murine IgG1 produced by hybridoma B72.3 (ATCC No. HB-8108). B72.3 is a first generation monoclonal antibody developed using a human breast carcinoma extract as the immunogen (see Colcher et al., Proc. Natl. Acad. Sci. (USA), 78:3199-3203 (1981); and U.S. Pat. Nos. 4,522,918 and 4,612,282 each of which is incorporated herein by reference). Other monoclonal antibodies directed against TAG-72 are designated "CC" (for colon cancer). As described by Schlom et al. (U.S. Pat. No. 5,512,443 which is incorporated herein by reference) CC monoclonal antibodies are a family of second generation murine monoclonal antibodies that were prepared using TAG-72 purified with B72.3. Because of their relatively good binding affinities to TAG-72, the following CC antibodies have been deposited at the ATCC, with restricted access having been requested: CC49 (ATCC No. HB 9459); CC 83 (ATCC No. HB 9453); CC46 (ATCC No. HB 9458); CC92 (ATTCC No. HB 9454); CC30 (ATCC No. HB 9457); CC11 (ATCC No. 9455); and CC15 (ATCC No. HB 9460). U.S. Pat. No. 5,512,443 further teaches that the disclosed antibodies may be altered into their chimeric form by substituting, e.g., human constant regions (Fc) domains for mouse constant regions by recombinant DNA techniques known in the art. Besides disclosing murine and chimeric anti-TAG-72 antibodies, Schlom et al. have also produced variants of a humanized CC49 antibody as disclosed in PCT/US99/25552 and single chain constructs as disclosed in U.S. Pat. No. 5,892,019 each of which is also incorporated herein by reference. Those skilled in the art will appreciate that each of the foregoing antibodies, constructs or recombinants, and variations thereof, may be synthetic and used to provide polypeptides in accordance with the present invention.

In addition to the anti-TAG-72 antibodies discussed above, various groups have also reported the construction and partial characterization of domain-deleted CC49 and B72.3 antibodies (e.g., Calvo et al. Cancer Biotherapy, 8(1):95-109 (1993), Slavin-Chiorini et al. Int. J. Cancer 53:97-103 (1993) and Slavin-Chiorini et al. Cancer. Res. 55:5957-5967 (1995).

In one embodiment, a donor antibody of the invention binds to the CD23 (U.S. Pat. No. 6,011,138). In a preferred embodiment, a donor antibody of the invention binds to the same epitope as the 5E8 antibody. In another embodiment, a donor antibody of the invention comprises at least one CDR from an anti-CD23 antibody, e.g., the 5E8 antibody.

In another embodiment, a donor antibody of the invention binds to the CRIPTO-I antigen (WO02/088170A2 or WO03/083041 A2). In certain embodiments, the antibodies of the invention specifically bind to Cripto. Cripto is a cell surface signaling protein capable of activating several different pathways, including a MAP kinase pathway (DeSantis et al., 1997, Cell Growth Differ. 8:1257-66; Kannan et al., 1997, J. Biol. Chem. 272:3330-35); the TGF-β pathway (Gritsman et al., 1999, Development 127:921-32; Schier et al., 2000, Nature 403:385-89); possible interactions with the Wnt pathway (Salomon et al., 2000, Endocr. Relat. Cancer. 7:199-226); and cross-talk with the EGF pathway (Bianco et al., 1999, J. Biol. Chem. 274:8624-29).

As used herein, Cripto includes the CR-1 Cripto protein, the CR-3 Cripto protein, and fragments thereof. Such fragments may be entire domains, such as the extracellular or intracellular domains, the EGF-like domain, the cys-rich domain, the receptor binding domain, and the like. Such fragments may also include contiguous and noncontiguous epitopes in any domain of the Cripto protein.

The 188 amino acid sequence for CR-1 is as follows (SEQ ID NO: 1):

MDCRKMARFSYSVIWIMAISKVFELGLVAGLGHQEFARPSRGYLAFRDDS

IWPQEEPAIRPRSSQRVPPMGIQHSKELNRTCCLNGGTCMLGSFCACPPS

FYGRNCEHDVRKENCGSVPHDTWLPKKCSLCKCWHGQLRCFPQAFLPGCD

GLVMDEHLVASRTPELPPSARTTTFMLVGICLSIQSYY

The 188 amino acid sequence for CR-3 is as follows (SEQ ID NO: 2):

MDCRKMVRFSYSVIWIMAISKAFELGLVAGLGHQEFARPSRGDLAFRDDS

IWPQEEPAIRPRSSQRVLPMGIQHSKELNRTCCLNGGTCMLESFCACPPS

FYGRNCEHDVRKENCGSVPHDTWLPKKCSLCKCWHGQLRCFPQAFLPGCD

GLVMDEHLVASRTPELPPSARTTTFMLAGICLSIQSYY

In specific embodiments, the anti-Cripto antibody CDRs optimized by the methods of the invention are those of the B3F6.17 anti-Cripto antibody (ATCC ACCESSION NO. PTA-3319). Expression and purification of anti-Cripto antibodies has been described in detail in PCT/US2002/011950, U.S. Pat. No. 5,792,616, U.S. Pat. No. 5,256,643, and US20040146940 the entire contents of which are hereby incorporated herein by reference. In other embodiments, a polypeptide of the invention binds to the same epitope as the B3F6 antibody. In still other embodiments, a polypeptide of the invention comprises at least one CDR from an anti-CRIPTO-I antibody, e.g., the B3F6 antibody.

In a preferred embodiment, a donor antibody employed in the methods of the invention binds to a cell-surface adhesion molecule. In certain embodiments, the antibodies of the invention specifically bind to an integrin. The integrins are a group of cell-extracellular matrix and cell-cell adhesion receptors exhibiting an alpha-beta heterodimeric structure, with a widespread cell distribution and a high degree of conservation throughout evolution. In particular embodiments, integrin to which the donor antibody binds is a member of the β1 integrin or VLA family, which includes at least six receptors that specifically interact with fibronectin, collagen, and/or laminin.

In particularly preferred embodiments, the antibody binds to the VLA-4 integrin (α4β1 integrin). VLA-4 is atypical because it is mostly restricted to lymphoid and myeloid cells (Hemler et al., 1987, J. Biol. Chem. 2:11478-11485), and indirect evidence had suggested that it might be involved in various cell-cell interactions within the immune system (Holtzmann et al., 1989, Cell 56:37-46). In addition, VLA-4 has been shown to mediate T and B lymphocyte attachment to the heparin II binding fragment of human plasma fibronectin (FN) (Wayner et al., 1989, J. Cell Biol. 109:1321-1330).

VLA-4 has been demonstrated to bind to VCAM-1. VCAM-1, like ICAM-1, is a member of the immunoglobulin gene superfamily (Osborn et al., 1989, Cell 59: 1203-1211)

which is expressed on vascular endothelium in response to cytokines and other inflammatory mediators, thereby facilitating lymphocyte recruitment to sites of infection and inflammation. VCAM-1 and VLA-4 were demonstrated to be a ligand-receptor pair that allows attachment of lymphocytes to activated endothelium by Elices et al., 1990 Cell 60:577-584. Thus, VLA-4 represents a singular example of a β1 integrin receptor participating in both cell-cell and cell-extracellular matrix adhesion functions by means of the defined ligands VCAM-1 and FN. Although VLA-4 is normally restricted to hematopoietic lineages, it is found on melanoma cell lines, and thus it has been suggested that VCAM1 may participate in metastasis of such tumors (Rice et al., 1989, Science, 246:1303-1306).

The apparent involvement of the VCAM1/VLA-4 adhesion pathway in infection, inflammation and possibly atherosclerosis has led to continuing intensive research to understand the mechanisms of cell-cell adhesion on a molecular level and has led investigators to propose intervention in this adhesion pathway as a treatment for diseases, particularly inflammation (Osborn et al., 1989 supra). Intervening with the ability of the VLA-4 to bind VCAM-1 using anti-VLA-4 antibodies has been shown to be effective method for treating a variety of inflammatory diseases such as, for example, Inflammatory Bowel Disease and asthma (see, for example, U.S. Pat. Nos. 5,932,214 and 5,871,734).

Exemplary monoclonal antibodies to VLA-4 have been described to date fall into several categories based on epitope mapping studies (Pulido et al., 1991, J. Biol. Chem., 266(16): 10241-10245). Importantly one particular group of antibodies, to epitope "B", are effective blockers of all VLA-4-dependent adhesive functions (Pulido et al., supra). The preparation of such monoclonal antibodies to epitope B of VLA 4, including, for example the HP1/2 MAb, have been described by Sanchez-Madrid et al., 1986, Eur. J. Immunol., 16:1343-1349.

In specific embodiments, the anti-VLA-4 antibody optimized by the methods of the invention is the murine HP1/2 anti-VLA-4 antibody described in U.S. Pat. No. 6,602,503. In another specific embodiment, the anti-VLA-4 antibody is a murine HP1/2 antibody having a heavy chain comprising the sequence of SEQ ID NO:19 and a light chain comprising the sequence of SEQ ID NO:26. Other anti-VLA-4 antibodies useful as donor antibodies in the methods of the invention include HP-2/1, HP-1/3, HP2/4, L25, 4B9, and P4C2 which are capable of recognizing the α chain of VLA-4. In preferred embodiments, the antibody will recognize epitope B of the VLA-4α4 chain (see Pulido et al. *J. Biol. Chem.*, 266(16); 10241-10245 (1991)).

Antibodies having similar specificity and having high binding affinities to VLA-4 comparable to that of HP 1/2, would be particularly promising candidates for the preparation of humanized recombinant anti-VLA-4 antibodies useful as assay reagents, diagnostics and therapeutics.

In one embodiment, a polypeptide of the invention comprises at least one CDR from an anti-VLA4 antibody, e.g., the HP1/2 antibody.

Still other embodiments of the present invention comprise modified antibodies that are derived from or bind to the same tumor associated antigen as C5E10. As set forth in co-pending application Ser. No. 09/104,717, C5E10 is an antibody that recognizes a glycoprotein determinant of approximately 115 kDa that appears to be specific to prostate tumor cell lines (e.g. DU145, PC3, or ND1). Thus, in conjunction with the present invention, polypeptides that specifically bind to the same tumor-associated antigen recognized by C5E10 antibodies could be used alone or conjugated with an effector moiety by the methods of the invention, thereby providing a modified polypeptide that is useful for the improved treatment of neoplastic disorders. In particularly preferred embodiments, a donor antibody will comprise all or part of the antigen binding region of the C5E10 antibody as secreted from the hybridoma cell line having ATCC accession No. PTA-865. The resulting polypeptide could then be conjugated to a therapeutic effector moiety as described below and administered to a patient suffering from prostate cancer in accordance with the methods herein.

In another embodiment, a donor antibody of the invention binds to CD40L. Generation of anti-CD154 (anti-CD40L) antibodies has been described in U.S. 60/591,337, the entire contents of which are hereby incorporated herein by reference. Crystal structure data for the 5c8 anti-CD154 antibody were obtained via crystallization and analysis of the CD40L/5c8 complex. The crystal structure of this CD40 ligand complexed with the Fab fragment of humanized neutralizing antibody 5c8 (PDB code: 1I9R) was prepared using standard procedures for adding hydrogens with the program CHARMM (Accelrys, Inc., San Diego, Calif.). N-acetamide and N-methylamide patches were applied to the N termini and C-termini, respectively. The crystal structure was solved to 3.1 Å at a pH of 6.50. Since CD40L is naturally a trimer, there are three 5c8 Fab molecules and 5 CD40L molecules in the complex. They form three independent CD40L/5c8 interfaces in the complex. A zinc (ZN) atom was bound to each of the 5c8 Fab and it was included into the calculation. Calculations were carried out independently for three interfaces.

In another embodiment, a donor antibody of the invention binds to MCP. Generation of anti-MCP antibody 11K2 has been described in PCT/US2003/037834, the entire contents of which are hereby incorporated herein by reference. 11K2 is a pan-MCP antibody and is specific for MCP-1, MCP-2 and MCP-3. In place of crystal structure data for the 11K2 antibody, a 3D structural model was generated based on the closest solved murine antibody structures for the heavy and light chains. For this purpose, an antibody designated 184.1 (Protein Data Bank (PDB) ID: 184.1) was chosen as a template for modeling the 11K2 light chain, and an antibody designated E8 (PDB ID: 1OPG) was chosen as the template for modeling the heavy chain. The model was further refined by a series of energy minimization steps to relieve unfavorable atomic contacts and optimize electrostatic and van der Waals interactions.

The computer model of the structure of an antibody, e.g., 11K2, can in turn serve as a starting point for predicting the three-dimensional structure of an antibody containing the 11K2 complementarity determining regions substituted in human framework structures. Additional models can be constructed representing the structure as further amino acid substitutions are introduced.

Three-dimensional structural information for some antibodies is publicly available, for example, from the Research Collaboratory for Structural Bioinformatics' Protein Data Bank (PDB). The PDB is freely accessible via the World Wide Web internet and is described by Berman et al. (2000) *Nucleic Acids Research*, 28:235. Computer modeling allows for the identification of CDR-interacting residues.

C. Acceptor Ig Variable Region Sequences

As set forth above, acceptor Ig variable region sequences need not be derived from antibodies which exist in nature. Although human antibody Ig variable region sequences may be chosen, other sequences, e.g., consensus sequences, germline sequences, and human sequences comprising amino acid modifications may also be selected.

In one embodiment, protein sequence databases of human variable domains may be searched with the donor variable domain sequence.

In one embodiment, the most suitable acceptor sequence(s) are selected by looking at overall sequence similarity, in particular sequence similarity at those positions whose amino acid sidechains sterically interact with any residues of the CDRs. These residues can be identified, e.g., by structural analysis of an x-ray structure or 3D homology model of the donor variable domain.

Alternatively, since the structure of antibodies is well-conserved, a list of residue positions that usually interact with the CDRs can be used, in which case it is not necessary to have a structural model. For example, a number of FR residues have been identified as "canonical" (Chothia C, Lesk A M. *J Mol Biol.* 196:901-17; Al-Lazikani B, et al. *J Mol Biol.* 273: 927-48) for particular CDR conformations, and the amino acids at these positions in the acceptor sequence should ideally be identical to those in the donor sequence. All but one (L1, L2, L3, H1, H2) of the six antibody CDRs have been found to correspond to a limited number of "canonical" conformational states, depending on the residue types of the canonical residues and the length of the individual CDRs.

Other criteria for selection of appropriate acceptor variable region sequences include physico-chemical properties such as stability, solubility, aggregation, and biological properties, such as expression levels in cells.

III. RATIONAL SELECTION OF VARIABLE REGION AMINO ACID RESIDUES FOR SUBSTITUTION

In the novel humanization approach described herein, the following basic steps are taken to construct a humanized antibody variable domain:

1. As set forth above, based on the known sequence of the donor antibody variable domain, an acceptor variable domain is selected.
2. Based on a x-ray structure or a structural model of the donor antibody variable domain, residue differences in the framework that are likely to affect the conformation of the CDRs in the potential grafted antibody are identified.
3. Using the donor CDRs as a template, new CDR sequences are designed that will accommodate the residue differences in the framework without affecting the CDR conformation.

The final sequence designs consist of an acceptor variable domain framework that is largely or completely unchanged, with CDRs that have been designed to "fit" the framework.

Step 2: Identification of Important Residue Differences

If no acceptor framework can be identified in which all important residues are identical to the donor framework, a list of the differences is made. It is important that multiple acceptor frameworks are considered, since the sequence with the fewest differences in the important residues is not necessarily the best acceptor candidate. For instance, if the most similar sequence has one difference (e.g., an ALA residue in the donor that is an ARG residue in the acceptor that involves a difference in charge) it can be a less suitable candidate than an acceptor sequence with two differences (e.g., LEU and SER to ILE and ALA, respectively).

The sequence differences in the framework that may affect CDR conformation are determined and nominated as a "flexible zone". All residues (most of them are in CDRs but some may be in a FR) that are adjacent to these identified residues are selected as a "mutation zone". If the 3D structure of the donor or acceptor antibody or antibody variable region is known, such a structure can be used in this analysis. Antibodies whose 3D structure has been analyzed fall into a limited number of structural or "canonical" classes based on the conformation of the CDRs. Five of the six CDRs (excluding H3) frequently fall into one of two to six of these canonical classes (Chothia and Lesk, 1987; Chothia et al., 1989). Canonical class members have similar backbone conformation, based on the presence of conserved canonical residues (in FR and CDR) which maintain CDR conformation (e.g., by hydrogen bonding, electrostatic, and hydrophobic interactions).

Thus, because acceptor canonical FR residues are important for maintaining CDR conformation, residue differences between donor and acceptor at these residue positions are important. Exemplary canonical residues include residues 2, 25, 27B, 28, 29, 30, 33, 48, 51, 52, 64, 71, 90, 94 and 95 of the light chain and residues 24, 26, 27 29, 34, 35, 35A, 52, 54, 55, 71 and 94 of the heavy chain (FR residues are underlined). Additional residues (e.g., CDR structure-determining residues) can be identified according to the methodology of Martin and Thornton (1996) *J. Mol. Biol.* 263:800. FR interface packing residues and unusual murine residues that are close to the binding site or, residues in the "Vernier Zone," which forms a platform on which the CDRs rest (Foote et al., J. Mol. Biol. 224, p. 487 (1992)), those close to peptide antigen, and those close to CDR H3 should be considered to be important residues.

The variable region 3D environment around each of the important acceptor FR amino acids that differs from the corresponding donor amino acid is determined to aid in design of CDRs to accommodate the FR differences between the donor and acceptor.

Step 3: Design of the CDRs

Using the list of important framework residue differences (also referred to herein as "flexible zone" residues), novel sequences are designed that will preserve the original conformation that the CDRs have in the donor antibody, in one embodiment, while maintaining most, if not all, acceptor framework residues.

To design the novel sequences, candidate amino acid residues for substitution are first identified. Candidate residues for substitution are amino acids that are adjacent to the framework residues (or flexible zone residues) designated as important according to step 2 above (also referred to herein as "mutation zone residues"). Although candidate residues (or mutation zone residues) necessarily include at least one CDR amino acid, in certain embodiments they may also include other framework residues that are adjacent to the flexible zone residues. Said candidate residues include those residues which are immediately adjacent to a flexible zone residue in the sequence or primary structure of the antibody chain, as well as those residues which are adjacent to the flexible zone residue in the tertiary or 3-D structure of the antibody chain. Such candidate residues can be identified based, e.g., on structure (as determined, for example, by xray or computer modeling) or can be made without a structure, for example using a database. Some exemplary methods are described in more detail below.

Proteins are known to fold into three-dimensional structures that are dictated by the sequences of their amino acids and by the solvent in which a given protein (or protein-containing complex) is provided. The three-dimensional structure of a protein influences its biological activity and stability, and that structure can be determined or predicted in a number of ways. X-ray crystallography is perhaps the best-known way of determining protein structure. In one embodiment, candidate amino acids can be identified (e.g. a CDR residue and, optionally, a FR residue) and potential changes to the candidate amino acids can be evaluated based on the existing crystal structure of an antibody or an antibody fragment, e.g., a Fab fragment. Numerous antibody crystal structures exist and can be found, e.g., using the Brookhaven Protein Databank or other private or public databases. If the crystal structure for a given acceptor or donor antibody or variable region does not exist, methods known in the art can be used to obtain the structure of an antibody, antibody variable region or antibody fragment, including a fragment consisting of, e.g., a single-chain antibody, Fab fragment, etc. A structure of an antigen-antibody complex may also be used. Methods for forming crystals of an antibody, an antibody fragment, or scFv-antigen complex have been reported by, for example, van den Elsen et al. (*Proc. Natl. Acad. Sci. USA* 96:13679-13684, 1999, which is expressly incorporated by reference herein).

Estimates of structure can also be made using circular dichroism, light scattering, or by measuring the absorption and emission of radiant energy. Other useful techniques include neutron diffraction and nuclear magnetic resonance (NMR). All of these methods are known to those of ordinary skill in the art, and they have been well described in standard textbooks (see, e.g., *Physical Chemistry*, 4th Ed., W. J. Moore, Prentiss-Hall, N.J., 1972, or *Physical Biochemistry*, K. E. Van Holde, Prentiss-Hall, N.J., 1971)) and numerous publications. Such techniques, although they yield only approximate data, can be carried out to inform one or more steps of the method of the invention.

Alternatively, tertiary structure can be predicted using model building of three-dimensional structures of one or more homologous proteins (or protein complexes) that have a known three-dimensional structure. This can be accomplished using, e.g., structure homology modeling in which the most similar heavy and light chain in a protein databank is used as a template to build a model of the antibody.

Alternatively, for ab initio modeling of CDRs a structural database is not necessary, rather structures are created based on certain algorithms. One example is the CONGEN conformation search method described by Broccoleri and Karplus (1987. Biopolymers 26:137-168).

Having selected candidate amino acids for substitution, the next step is to redesign the variable region sequence by electing an amino acid that will replace the candidate amino acid. As described above, the elected amino acid is a residue that will conformationally accommodate the flexible zone residue(s), thereby preserving the original conformation that the CDRs have in the donor antibody. In certain embodiments, wherein the candidate amino acid(s) are all CDR residues, substitution of the candidate amino acid residue(s) with an elected amino will preserve all of the human framework residues from the acceptor variable region. In other embodiments, wherein the candidate amino acid(s) include a framework residue, all residues in the framework region outside of the mutation zone are preserved as human.

An exemplary approach to redesigning the variable region sequences (e.g. CDR sequences, and optionally FR sequences) is by using structure-based computational design methods. The identity of the residues in the flexible zone is fixed to acceptor residues, but their 3D positions are allowed to change during the calculation. The residues in the mutation zone are allowed to change both their amino acid identity and conformation. All residues in the CDRs outside of the mutation zone are donor, and all residues in the FR outside of the mutation zone are acceptor. In this method, the candidate residues (e.g. CDR residues, and optionally FR residues) that have sidechains that are geometrically close (e.g. within about 4-25 Å of such regions, in particular <5 Angstroms distance) to one or more of the important residue differences in the framework (as identified in step 2), are simultaneously mutated computationally to all possible 3D conformations (rotamers) of any of the 20 naturally occurring amino acids and the resulting mutants are evaluated computationally. One such method is known as sidechain repacking method. In a sidechain repacking calculation, the candidate amino acid residues can be modified computationally, and the stability of the resulting polypeptide mutants evaluated computationally. The sidechain repacking calculation generates a ranked list of the variants that have altered stability (i.e., altered intramolecular energy). Mutants which result in low free energy, and which are confirmed as conformationally accommodating by visual inspection of a 3-D model, can then be selected for experimental expression. The list of computationally generated mutants can be sorted by calculated stability of the mutant in order to generate a list of variants that will be expressed experimentally. In the calculations the protein backbone is allowed very little or no flexibility, which ensures that the designed mutants are predicted to be stable with the given CDR conformations. Thus, the computational analysis allows one to predict structurally compatible sequences, in particular CDR sequences, with given FR domains within a variable region.

The number of protein mutants that is evaluated computationally can be very large, since every variable amino acid position can be mutated into all 20 standard amino acids or a subset of 20 amino acids (e.g. polar or nonpolar amino acids, small or large side-chain amino acids, sterically-hindered or flexible amino acids). Exemplary computational algorithms used to perform energy evaluations to rank the results of the computational analysis include dead-end elimination and tree search algorithms (see for example, Lasters et al. (*Protein Eng.* 8:815-822, 1995), Looger and Hellinga (*J. Mol. Biol.* 307:429-445, 2001), and Dahiyat and Mayo (*Protein Sci.* 5:895-903, 1996)), Monte Carlo search and Simulated Annealing (Kuhlman B et al., *Science*, 2003, 302(5649):1364-8; Ambroggio X I, et al., *J. Am. Chem. Soc.*, 2006, 128(4): 1154-61), Free Energy Calculation (Almolf M, et al., *Biophys. J.*, 2006, 90(2):433-42), and Exhaustive Conformational Sampling (Green D F, et al., ICE (Integrated Continuum Electrostatics) software package, MIT, 2003).

In yet another embodiment, a database (e.g., in the form of a table) with known antibody sequences that correspond to specific canonical states of the CDRs can be made. For instance, suppose the donor antibody has a L3 CDR loop of canonical state 1, and the acceptor sequence has a framework residue difference (at position x) that sterically interacts with loop L3. In this case the table will be searched for other antibodies with the L3 loop in canonical state 1 in which residue x is identical or similar to the acceptor sequence. As used in this context, the term "similar to" means similar in physicochemical properties to.

For example, assume that such an antibody is found (antibody z). If the sequence of the residue(s) in the L3 loop of antibody z that contact (or interact with) residue x differs from the corresponding residues in the donor L3 loop, the L3 loop can be redesigned by incorporating these sequence changes. In essence, if nature has found a way to produce a given canonical loop conformation with different residues at the CDR-framework interface, that information can be used to preserve the canonical loop conformation in the humanized antibody. Examples of "similar" amino acid residues include Glycine and Alanine; Valine, Leucine, and Isoleucine; Phenylalanine and Tyrosine; Serine and Threonine; Aspartate and Glutamate; Asparagine and Glutamine.

In yet another embodiment, both the computational structure-based and database-based methods described above can be used iteratively or in combination. In an exemplary embodiment, the alteration of at least one candidate amino acid residue (e.g., a CDR residue, and optionally a FR residue) is performed using one method (e.g. a computational based method described supra), followed by alteration of at least one second candidate amino acid residue (e.g. a donor CDR residue and/or FR amino acid residue using another method (e.g., database methods described supra).

In one embodiment, the methods of the invention may include an output device that displays information to a user (e.g., a CRT display, an LCD, a printer, a communication device such as a modem, audio output, and the like). In addition, instructions for carrying out the method, in part or in whole, can be conferred to a medium suitable for use in an electronic device for carrying out the instructions. Thus, the methods of the invention are amendable to a high throughput approach comprising software (e.g., computer-readable instructions) and hardware (e.g., computers, robotics, and chips). The computer-implemented process is not limited to a particular computer platform, particular processor, or particular high-level programming language.

In one embodiment, the process may be iterative, e.g., involving initial alteration of a candidate amino acid residue (e.g. one donor CDR and/or FR amino acid residue), followed by affinity testing, structural determination, etc., and subsequent rounds of alteration of the same or different amino acid residues. To practice the present invention, such alterations may be modeled (e.g., made in silico) and/or, in some embodiments, performed and expressed as a polypeptide.

IV. METHODS OF MAKING HUMANIZED IG VARIABLE REGIONS OF DESIRED SEQUENCE

Having arrived at a desired mutation to make in donor CDR, one can use any of a variety of available methods to produce a humanized antibody comprising the mutation.

Such polypeptides can, for example, be synthesized using techniques known in the art. Alternatively nucleic acid molecules encoding the desired variable regions can be synthesized and the polypeptides produced by recombinant methods.

For example, once the sequence of a humanized variable region has been decided upon, that variable region or a polypeptide comprising it can be made by techniques well known in the art of molecular biology. More specifically, recombinant DNA techniques can be used to produce a wide range of polypeptides by transforming a host cell with a nucleic acid sequence (e.g., a DNA sequence that encodes the desired variable region (e.g., a modified heavy or light chain; the variable domains thereof, or other antigen-binding fragments thereof)).

In one embodiment, the CDRs of the donor antibody can be altered prior to their incorporation into the acceptor framework.

In another embodiment, the art recognized process of CDR grafting can be used to transfer donor CDRs into acceptor FR. In most cases all three CDRs from the heavy chain are transplanted from the donor antibody to a single acceptor framework and all three CDRs from the light chain are transplanted to a different acceptor framework. It is expected that it should not always be necessary to transplant all the CDRs, as some CDRs may not be involved in binding to antigen, and CDRs with different sequences (and the same length) can have the same folding (and therefore contacts from antigen to the main chain contacts could be retained despite the different sequences). Indeed single domains (Ward et al, 1989, Nature 341, pp. 544-546) or even single CDRs (R. Taub et al, 1989, J. Biol Chem 264, pp. 259-265) can have antigen binding activities alone. However, whether all or only some of the CDRs are transplanted, the intention of CDR grafting is to transplant the same, or much the same antigen binding site, from animal to human antibodies (see, e.g., U.S. Pat. No. 5,225,539 (Winter)).

In one embodiment, one can prepare an expression vector including a promoter that is operably linked to a DNA sequence that encodes at least $V_H$ or $V_L$. If necessary, or desired, one can prepare a second expression vector including a promoter that is operably linked to a DNA sequence that encodes the complementary variable domain (i.e., where the parent expression vector encodes $V_H$, the second expression vector encodes $V_L$ and vice versa). A cell line (e.g., an immortalized mammalian cell line) can then be transformed with one or both of the expression vectors and cultured under conditions that permit expression of the chimeric variable domain or chimeric antibody (see, e.g., International Patent Application No. PCT/GB85/00392 to Neuberger et. al.).

In one embodiment, variable regions comprising donor CDRs and acceptor FR amino acid sequences can be made and then changes introduced into the nucleic acid molecules to effect the CDR amino acid substitution.

Exemplary art recognized methods for making a nucleic acid molecule encoding an amino acid sequence variant of a polypeptide include, but are not limited to, preparation by site-directed (or oligonucleotide-mediated) mutagenesis, PCR mutagenesis, and cassette mutagenesis of an earlier prepared DNA encoding the polypeptide.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the parent DNA is altered by first hybridizing an oligonucleotide encoding the desired mutation to a single strand of such parent DNA. After hybridization, a DNA polymerase is used to synthesize an entire second strand, using the hybridized oligonucleotide as a primer, and using the single strand of the parent DNA as a template. Thus, the oligonucleotide encoding the desired mutation is incorporated in the resulting double-stranded DNA.

PCR mutagenesis is also suitable for making amino acid sequence variants of polypeptides. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the DNA to be mutated. The codon(s) in the parent DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA encoding the polypeptide. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

A variable region generated by the methods of the invention can be re-modeled and further altered to further increase antigen binding. Thus, the steps described above can be preceded or followed by additional steps, including, e.g. affinity maturation. In addition, empirical binding data can be used to inform further optimization.

It will be understood by one of ordinary skill in the art that the polypeptides of the invention may further be modified such that they vary in amino acid sequence, but not in desired activity. For example, additional nucleotide substitutions leading to amino acid substitutions at "non-essential" amino acid residues may be made to the protein. For example, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members, i.e., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Aside from amino acid substitutions, the present invention contemplates other modifications, e.g., to Fc region amino acid sequences in order to generate an Fc region variant with altered effector function. One may, for example, delete one or more amino acid residues of the Fc region in order to reduce or enhance binding to an FcR. In one embodiment, one or more of the Fc region residues can be modified in order to generate such an Fc region variant. Generally, no more than one to about ten Fc region residues will be deleted according to this embodiment of the invention. The Fc region herein comprising one or more amino acid deletions will preferably retain at least about 80%, and preferably at least about 90%, and most preferably at least about 95%, of the starting Fc region or of a native sequence human Fc region.

One may also make amino acid insertion Fc region variants, which variants have altered effector function. For example, one may introduce at least one amino acid residue (e.g. one to two amino acid residues and generally no more than ten residues) adjacent to one or more of the Fc region positions identified herein as impacting FcR binding. By "adjacent" is meant within one to two amino acid residues of a Fc region residue identified herein. Such Fc region variants may display enhanced or diminished FcRn binding.

Such Fc region variants will generally comprise at least one amino acid modification in the Fc region. In one embodiment amino acid modifications may be combined. For example, the variant Fc region may include two, three, four, five, etc substitutions therein, e.g. of the specific Fc region positions identified herein. In another embodiment, a polypeptide may have altered binding to FcRn and to another Fc receptor.

V. EXPRESSION OF POLYPEPTIDES COMPRISING HUMANIZED IG VARIABLE REGIONS

In one embodiment, the polypeptides of the invention, e.g., humanized Ig variable regions and/or polypeptides comprising humanized Ig variable regions may be produced by recombinant methods. For example, a polynucleotide sequence encoding a polypeptide can be inserted in a suitable expression vector for recombinant expression. Where the polypeptide is an antibody, polynucleotides encoding additional light and heavy chain variable regions, optionally linked to constant regions, may be inserted into the same or different expression vector. An affinity tag sequence (e.g. a His(6) tag) may optionally be attached or included within the polypeptide sequence to facilitate downstream purification. The DNA segments encoding immunoglobulin chains are the operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the polypeptide.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species.

Other microbes, such as yeast, are also useful for expression. *Saccharomyces* and *Pichia* are exemplary yeast hosts, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

In addition to microorganisms, mammalian tissue culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, 293 cells, myeloma cell lines, transformed B-cells, and hybridomas. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

The subject polypeptide can also be incorporated in transgenes for introduction into the genome of a transgenic animal and subsequent expression, e.g., in the milk of a transgenic animal (see, e.g., Deboer et al. U.S. Pat. No. 5,741,957; Rosen U.S. Pat. No. 5,304,489; and Meade U.S. Pat. No. 5,849,992. Suitable transgenes include coding sequences for light and/or heavy chains in operable linkage with a promoter and enhancer from a mammary gland specific gene, such as casein or beta lactoglobulin.

Polypeptides (e.g., polypeptides) can be expressed using a single vector or two vectors. For example, antibody heavy and light chains may be cloned on separate expression vectors and co-transfected into cells.

In one embodiment, signal sequences may be used to facilitate expression of polypeptides of the invention.

Once expressed, the polypeptides can be purified according to standard procedures of the art, including ammonium sulfate precipitation, affinity columns (e.g., protein A or protein G), column chromatography, HPLC purification, gel electrophoresis and the like (see generally Scopes, Protein Purification (Springer-Verlag, N.Y., (1982)).

Either the humanized Ig variable regions or polypeptides comprising them can be expressed by host cells or cell lines in culture. They can also be expressed in cells in vivo. The cell line that is transformed (e.g., transfected) to produce the altered antibody can be an immortalized mammalian cell line, such as those of lymphoid origin (e.g., a myeloma, hybridoma, trioma or quadroma cell line). The cell line can also include normal lymphoid cells, such as B-cells, that have been immortalized by transformation with a virus (e.g., the Epstein-Barr virus).

Although typically the cell line used to produce the polypeptide is a mammalian cell line, cell lines from other sources (such as bacteria and yeast) can also be used. In particular, *E. coli*-derived bacterial strains can be used, especially, e.g., phage display.

Some immortalized lymphoid cell lines, such as myeloma cell lines, in their normal state, secrete isolated Ig light or heavy chains. If such a cell line is transformed with a vector that expresses an altered antibody, prepared during the process of the invention, it will not be necessary to carry out the remaining steps of the process, provided that the normally secreted chain is complementary to the variable domain of the Ig chain encoded by the vector prepared earlier.

If the immortalized cell line does not secrete or does not secrete a complementary chain, it will be necessary to introduce into the cells a vector that encodes the appropriate complementary chain or fragment thereof.

In the case where the immortalized cell line secretes a complementary light or heavy chain, the transformed cell line may be produced for example by transforming a suitable bacterial cell with the vector and then fusing the bacterial cell with the immortalized cell line (e.g., by spheroplast fusion). Alternatively, the DNA may be directly introduced into the immortalized cell line by electroporation.

In one embodiment, a humanized Ig variable region of the invention can be present in an antigen-binding fragment of any antibody. The fragments can be recombinantly produced and engineered, synthesized, or produced by digesting an antibody with a proteolytic enzyme. For example, the fragment can be an Fab fragment; digestion with papain breaks the antibody at the region, before the inter-chain (i.e., $V_H$-$V_H$) disulphide bond, that joins the two heavy chains. This results in the formation of two identical fragments that contain the light chain and the $V_H$ and $C_H1$ domains of the heavy chain. Alternatively, the fragment can be an F(ab')$_2$ fragment. These fragments can be created by digesting an antibody with pepsin, which cleaves the heavy chain after the inter-chain disulfide bond, and results in a fragment that contains both antigen-binding sites. Yet another alternative is to use a "single chain" antibody. Single-chain Fv (scFv) fragments can be constructed in a variety of ways. For example, the C-terminus of $V_H$ can be linked to the N-terminus of $V_L$. Typically, a linker (e.g., (GGGGS)$_4$) (SEQ ID NO: 29) is placed between $V_H$ and $V_L$. However, the order in which the chains can be linked can be reversed, and tags that facilitate detection or purification (e.g., Myc-, His-, or FLAG-tags) can be included (tags such as these can be appended to any antibody or antibody fragment of the invention; their use is not restricted to scFv). Accordingly, and as noted below, tagged antibodies are within the scope of the present invention. In alternative embodiments, the antibodies used in the methods described herein, or generated by those methods, can be heavy chain dimers or light chain dimers. Still further, an antibody light or heavy chain, or portions thereof, for example, a single domain antibody (DAb), can be used.

In another embodiment, a humanized Ig variable region of the invention is present in a single chain antibody (ScFv) or a minibody (see e.g., U.S. Pat. No. 5,837,821 or WO 94/09817A1). Minibodies are dimeric molecules made up of two polypeptide chains each comprising an ScFv molecule (a single polypeptide comprising one or more antigen binding sites, e.g., a $V_L$ domain linked by a flexible linker to a $V_H$ domain fused to a CH3 domain via a connecting peptide). ScFv molecules can be constructed in a $V_H$-linker-$V_L$ orientation or $V_L$-linker-$V_H$ orientation. The flexible hinge that links the $V_L$ and $V_H$ domains that make up the antigen binding site preferably comprises from about 10 to about 50 amino acid residues. An exemplary connecting peptide for this purpose is (Gly4Ser)3 (SEQ ID NO: 30) (Huston et al. (1988). PNAS, 85:5879). Other connecting peptides are known in the art.

Methods of making single chain antibodies are well known in the art, e.g., Ho et al. (1989), Gene, 77:51; Bird et al. (1988), Science 242:423; Pantoliano et al. (1991), Biochemistry 30:10117; Milenic et al. (1991), Cancer Research, 51:6363; Takkinen et al. (1991), Protein Engineering 4:837.

Minibodies can be made by constructing an ScFv component and connecting peptide-CH$_3$ component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis. In one embodiment, a minibody of the invention comprises a connecting peptide. In one embodiment, the connecting peptide comprises a Gly/Ser linker, e.g., GGGSSGGGSGG (SEQ ID NO: 31).

In another embodiment, a tetravalent minibody can be constructed. Tetravalent minibodies can be constructed in the same manner as minibodies, except that two ScFv molecules are linked using a flexible linker, e.g., having an amino acid sequence (G4S)$_4$G3AS (SEQ ID NO: 32).

In another embodiment, a humanized variable region of the invention can be present in a diabody. Diabodies are similar to scFv molecules, but usually have a short (less than 10 and preferably 1-5) amino acid residue linker connecting both variable domains, such that the V$_L$ and V$_H$ domains on the same polypeptide chain can not interact. Instead, the V$_L$ and V$_H$ domain of one polypeptide chain interact with the V$_H$ and V$_L$ domain (respectively) on a second polypeptide chain (WO 02/02781).

In another embodiment, a humanized variable region of the invention can be present in an immunoreactive fragment or portion of an antibody (e.g. an scFv molecule, a minibody, a tetravalent minibody, or a diabody) operably linked to an FcR binding portion. In an exemplary embodiment, the FcR binding portion is a complete Fc region.

VI. ANALYSIS OF AFFINITY

Preferably, the humanization methods described herein result in Ig variable regions in which the affinity for antigen is not substantially changed compared to the donor antibody.

In one embodiment, polypeptides comprising the variable domains of the instant invention bind to antigens with a binding affinity greater than (or equal to) about $10^5$, $10^6$, $10^7$, $10^8$, $10^9$, or $10^{10}$M$^{-1}$, (including affinities intermediate of these values).

Affinity, avidity, and/or specificity can be measured in a variety of ways. Generally, and regardless of the precise manner in which affinity is defined or measured, the methods of the invention improve antibody affinity when they generate an antibody that is superior in any aspect of its clinical application to the antibody (or antibodies) from which it was made (for example, the methods of the invention are considered effective or successful when a modified antibody can be administered at a lower dose or less frequently or by a more convenient route of administration than an antibody (or antibodies) from which it was made).

More specifically, the affinity between an antibody and an antigen to which it binds can be measured by various assays, including, e.g., an ELISA assay, a BiaCore assay or the KinExA™ 3000 assay (available from Sapidyne Instruments (Boise, Id.)). The ELISA assay was used to measure the affinities of anti-VLA-4 antibodies (see Example 3 below). Briefly, sepharose beads are coated with antigen (the antigen used in the methods of the invention can be any antigen of interest (e.g., a cancer antigen; a cell surface protein or secreted protein; an antigen of a pathogen (e.g., a bacterial or viral antigen (e.g., an HIV antigen, an influenza antigen, or a hepatitis antigen)), or an allergen) by covalent attachment. Dilutions of antibody to be tested are prepared and each dilution is added to the designated wells on a plate. A detection antibody (e.g. goat anti-human IgG HRP conjugate) is the added to each well followed by a chromagenic substrate (, e.g. HRP). The plate is then read in ELISA plate reader at 450 nM, and EC50 values are calculated. (It is understood, however, that the methods described here are generally applicable; they are not limited to the production of antibodies that bind any particular antigen or class of antigens.)

Those of ordinary skill in the art will recognize that determining affinity is not always as simple as looking at a single FIGURE. Since antibodies have two arms, their apparent affinity is usually much higher than the intrinsic affinity between the variable region and the antigen (this is believed to be due to avidity). Intrinsic affinity can be measured using scFv or Fab fragments.

VII. FUNCTIONALIZATION OF POLYPEPTIDES COMPRISING HUMANIZED IG VARIABLE REGIONS

Polypeptides comprising humanized Ig variable regions may be functionalized for a desired effect. For example, in certain embodiments, the polypeptides may be modified (e.g. by chemical or genetic means) by conjugation (ie. physically linked) to an additional moiety, e.g., a functional moiety such as, for example, a PEGylation moiety, a blocking moiety, a detectable moiety, a diagnostic moiety, and/or a therapeutic moiety, that serves to improve the desired function (e.g. therapeutic efficacy) of the polypeptide. Chemical conjugation may be performed by randomly or by site-specific modification of particular residues within the polypeptide. Exemplary functional moieties are first described below followed by useful chemistries for linking such functional moieties to different amino acid side chain chemistries of an polypeptide.

a) Functional Moieties

Examples of useful functional moieties include, but are not limited to, a PEGylation moiety, a blocking moiety, detectable moiety, a diagnostic moiety, and a therapeutic moiety.

Exemplary PEGylation moieties include moieties of polyalkylene glycol moiety, for example, a PEG moiety and preferably a PEG-maleimide moiety. Preferred pegylation moieties (or related polymers) can be, for example, polyethylene glycol ("PEG"), polypropylene glycol ("PPG"), polyoxyethylated glycerol ("POG") and other polyoxyethylated polyols, polyvinyl alcohol ("PVA) and other polyalkylene oxides, polyoxyethylated sorbitol, or polyoxyethylated glucose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. PEG is useful in biological applications for several reasons. PEG typically is clear, colorless, odorless, soluble in water, stable to heat, inert to many chemical agents, does not hydrolyze, and is nontoxic.

Preferably PEGylation moieties are attached to altered Fc-containing polypeptides of the invention that have enhanced-life. A PEGylation moiety can serve to further enhance the half-life of the polypeptide by increasing the molecule's apparent molecular weight. The increased apparent molecular weight reduces the rate of clearance from the body following subcutaneous or systemic administration. In many cases, a PEGylation also serve to decrease antigenicity and immunogenicity. In addition, PEGylation can increase the solubility of the polypeptide.

Exemplary blocking moieties include cysteine adducts, cystine, mixed disulfide adducts, or other compounds of sufficient steric bulk and/or charge such that antigen-dependent effector function is reduced, for example, by inhibiting the ability of the Fc region to bind an Fc receptor or complement protein. Preferably, said blocking moieties are conjugated to polypeptides of the invention with reduced effector function such that effector function is further reduced.

Exemplary detectable moieties which may be useful for conjugation to the polypeptides of the invention include fluorescent moieties, radioisotopic moieties, radiopaque moieties, and the like, e.g. detectable labels such as biotin, fluorophores, chromophores, spin resonance probes, or radiolabels. Exemplary fluorophores include fluorescent dyes (e.g. fluorescein, rhodamine, and the like) and other luminescent molecules (e.g. luminal). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei ($^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like). Other useful moieties are known in the art.

Examples of diagnostic moieties which may be useful for conjugation to the polypeptides of the invention include detectable moieties suitable for revealing the presence of a disease or disorder. Typically a diagnostic moiety allows for determining the presence, absence, or level of a molecule, for example, a target peptide, protein, or proteins, that is associated with a disease or disorder. Such diagnostics are also suitable for prognosing and/or diagnosing a disease or disorder and its progression.

Examples of therapeutic moieties which may be useful for conjugation to the polypeptides of the invention include, for example, anti-inflammatory agents, anti-cancer agents, anti-neurodegenerative agents, and anti-infective agents. The functional moiety may also have one or more of the above-mentioned functions.

Exemplary therapeutics include radionuclides with high-energy ionizing radiation that are capable of causing multiple strand breaks in nuclear DNA, and therefore suitable for inducing cell death (e.g., of a cancer). Exemplary high-energy radionuclides include: $^{90}Y$, $^{125}I$, $^{131}I$, $^{123}I$, $^{111}In$, $^{105}Th$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic.

Exemplary therapeutics also include cytotoxic agents such as cytostatics (e.g. alkylating agents, DNA synthesis inhibitors, DNA-intercalators or cross-linkers, or DNA-RNA transcription regulators), enzyme inhibitors, gene regulators, cytotoxic nucleosides, tubulin binding agents, hormones and hormone antagonists, anti-angiogenesis agents, and the like.

Exemplary therapeutics also include alkylating agents such as the anthracycline family of drugs (e.g. adriamycin, caminomycin, cyclosporin-A, chloroquine, methopterin, mithramycin, porfiromycin, streptonigrin, porfiromycin, anthracenediones, and aziridines). In another embodiment, the chemotherapeutic moiety is a cytostatic agent such as a DNA synthesis inhibitor. Examples of DNA synthesis inhibitors include, but are not limited to, methotrexate and dichloromethotrexate, 3-amino-1,2,4-benzotriazine 1,4-dioxide, aminopterin, cytosine β-D-arabinofuranoside, 5-fluoro-5'-deoxyuridine, 5-fluorouracil, ganciclovir, hydroxyurea, actinomycin-D, and mitomycin C. Exemplary DNA-intercalators or cross-linkers include, but are not limited to, bleomycin, carboplatin, carmustine, chlorambucil, cyclophosphamide, cis-diammineplatinum(II) dichloride (cisplatin), melphalan, mitoxantrone, and oxaliplatin.

Exemplary therapeutics also include transcription regulators such as actinomycin D, daunorubicin, doxorubicin, homoharringtonine, and idarubicin. Other exemplary cytostatic agents that are compatible with the present invention include ansamycin benzoquinones, quinonoid derivatives (e.g. quinolones, genistein, bactacyclin), busulfan, ifosfamide, mechlorethamine, triaziquone, diaziquone, carbazilquinone, indoloquinone E09, diaziridinyl-benzoquinone methyl DZQ, triethylenephosphoramide, and nitrosourea compounds (e.g. carmustine, lomustine, semustine).

Exemplary therapeutics also include cytotoxic nucleosides such as, for example, adenosine arabinoside, cytarabine, cytosine arabinoside, 5-fluorouracil, fludarabine, floxuridine, ftorafur, and 6-mercaptopurine; tubulin binding agents such as taxoids (e.g. paclitaxel, docetaxel, taxane), nocodazole, rhizoxin, dolastatins (e.g. Dolastatin-10, -11, or -15), colchicine and colchicinoids (e.g. ZD6126), combretastatins (e.g. Combretastatin A-4, AVE-6032), and vinca alkaloids (e.g. vinblastine, vincristine, vindesine, and vinorelbine (navelbine)); anti-angiogenesis compounds such as Angiostatin K1-3, DL-α-difluoromethyl-ornithine, endostatin, fumagillin, genistein, minocycline, staurosporine, and (±)-thalidomide.

Exemplary therapeutics also include hormones and hormone antagonists, such as corticosteroids (e.g. prednisone), progestins (e.g. hydroxyprogesterone or medroprogesterone), estrogens, (e.g. diethylstilbestrol), antiestrogens (e.g. tamoxifen), androgens (e.g. testosterone), aromatase inhibitors (e.g. aminogluthetimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-α, rapamycin, sex hormone-binding globulin, and thapsigargin.

Exemplary therapeutics also include enzyme inhibitors such as, S(+)-camptothecin, curcumin, (−)-deguelin, 5,6-dichlorobenz-imidazole ribofuranoside, etoposide, formestane, fostriecin, hispidin, 2-imino-1-imidazolidineacetic acid (cyclocreatine), mevinolin, trichostatin A, tyrphostin AG 34, and tyrphostin AG 879.

Exemplary therapeutics also include gene regulators such as 5-aza-2'-deoxycytidine, 5-azacytidine, cholecalciferol (vitamin $D_3$), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Exemplary therapeutics also include cytotoxic agents such as, for example, the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like.

Still other cytotoxins that are compatible with the teachings herein include auristatins (e.g. auristatin E and monomethylauristan E), calicheamicin, gramicidin D, maytansanoids (e.g. maytansine), neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, and analogs or homologs thereof.

Other types of functional moieties are known in the art and can be readily used in the methods and compositions of the present invention based on the teachings contained herein.

b) Chemistries for Linking Functional Moieties to Amino Acid Side Chains

Chemistries for linking the foregoing functional moieties be they small molecules, nucleic acids, polymers, peptides, proteins, chemotherapeutics, or other types of molecules to particular amino acid side chains are known in the art (for a detailed review of specific linkers see, for example, Hermanson, G. T., *Bioconjugate Techniques*, Academic Press (1996)).

Exemplary art recognized linking groups for sulfhydryl moieties (e.g., cysteine, or thiol side chain chemistries) include, but are not limited to, activated acyl groups (e.g., alpha-haloacetates, chloroacetic acid, or chloroacetamide), activated alkyl groups, Michael acceptors such as maleimide or acrylic groups, groups which react with sulfhydryl moieties via redox reactions, and activated di-sulfide groups. The sulfhydryl moieties may also be linked by reaction with bromotrifluoroacetone, alpha-bromo-beta-(5-imidazoyl)propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

In a preferred embodiment, a cysteine or other amino acid with thiol side chain chemistry is linked during or subsequent to the production of an Fc containing polypeptide. For example, when producing the modified Fc containing polypeptide using cell culture, conditions are provided such that a free cysteine in solution can form a cysteine adduct with the thiol side chain of the Fc containing polypeptide. The so formed adduct may be used to inhibit glycosylation and/or effector function, or, subsequently subjected to reducing conditions to remove the adduct and thereby allow for the use of one of the aforementioned sulfhydryl chemistries.

Exemplary art recognized linking groups for hydroxyl moieties (e.g., serine, threonine, or tyrosine side chain chemistries) include those described above for sulfhydryl moieties including activated acyl groups, activated alkyl groups, and Michael acceptors.

Exemplary art recognized linking groups for amine moieties (e.g., asparagine or arginine side chain chemistries) include, but are not limited to, N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl, 3-carboxy-4-nitrophenyl, imidoesters (e.g., methyl picolinimidate), pyridoxal phosphate, pyridoxal, chloroborohydride, trinitrobenzenesulfonic acid, O-methyliosurea, and 2,4-pentanedione.

Exemplary art recognized linking groups for acidic moieties (e.g., aspartic acid or glutamic side chain chemistries) include activated esters and activated carbonyls. Acidic moieties can also be selectively modified by reaction with carbodiimides (R'N—C—N—R') such as 1-cyclohexyl-3-[2-morpholinyl-(4-ethyl)]carbodiimide or 1-ethyl-3-(4-azonia-4,4-dimethylpentyl)carbodiimide.

Where the functional moiety desired is a PEGylation moiety, PEGylation reactions which are well known in the art may be employed. For example, in one method, the PEGylation is carried out via an acylation reaction or an alkylation reaction with a reactive polyethylene glycol molecule (or an analogous reactive water-soluble polymer). A water-soluble polymer for pegylation of the antibodies and antibody fragments of the invention is polyethylene glycol (PEG). In another embodiment, the polymer for pegylation is polyethylene glycol-maleimide (i.e., PEG-maleimide).

Methods for preparing pegylated antibodies and antibody fragments of the invention will generally comprise the steps of a) reacting the antibody or antibody fragment with polyethylene glycol, such as a reactive ester or aldehyde derivative of PEG, under conditions whereby the antibody or antibody fragment becomes attached to one or more PEG groups, and b) obtaining the reaction products. It will be apparent to one of ordinary skill in the art to select the optimal reaction conditions or the acylation reactions based on known parameters and the desired result. In one embodiment, a particular amino acid reside can be targeted, for example, the first amino acid residue altered in order to inhibit glycosylation of a second amino acid residue, and preferably where the first amino acid is a cysteine or has a thiol chemistry.

VIII. PROPHYLACTIC, DIAGNOSTIC, AND THERAPEUTIC METHODS

The present invention has general utility when humanized variable domain or a polypeptide comprising such a domain (e.g., an antibody or fusion protein) binds an antigen, where the binding provokes a desired response. One example of an effector-mediated response is the reduction in the root cause of a disorder (e.g., elimination of tumor cells or of antigen-bearing cells that are involved in immune or inflammatory responses). In another embodiment, one or more symptom(s) of a disorder can be reduced. In another embodiment, the compositions described herein can be used to alter an effector-mediated response in a diagnostic reagent (e.g., an antibody used for imaging tumors).The methods described herein can be used to treat a subject at risk of developing a disorder or a subject currently exhibiting symptoms of a disorder.

A. Anti-Tumor Therapy

Accordingly, in certain embodiments, a polypeptide of the present invention is useful in the prevention or treatment of cancer. In one embodiment, an polypeptide blocks autocrine or paracrine growth (e.g., by binding to a receptor without transducing a signal, or by binding to a growth factor). In preferred embodiments, the polypeptide is capable of binding to a tumor-associated antigen.

In one embodiment, the polypeptides may reduce tumor size, inhibit tumor growth and/or prolong the survival time of tumor-bearing animals. In general, the disclosed invention may be used to prophylactically or therapeutically treat any neoplasm comprising an antigenic marker that allows for the targeting of the cancerous cells by the modified antibody. Exemplary cancers or neoplasias that may be prevented or treated include, but are not limited to bladder cancer, breast cancer, head and neck cancer, prostate cancer, colo-rectal cancer, melanoma or skin cancer, breast cancer, ovarian cancer, cervical cancer, endometrial cancer, kidney cancer, lung cancer (e.g. small cell and non-squamos cell cancers), pancreatic cancer, and multiple myeloma. More particularly, the modified antibodies of the instant invention may be used to treat Kaposi's sarcoma, CNS neoplasias (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the ovary, Wilm's tumor or small cell lung carcinoma. It will be appreciated that appropriate antibodies may be obtained for tumor associated antigens related to each of the forgoing neoplasias without undue experimentation using the instant disclosure or other techniques known in the art.

Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the polypeptides and methods of the present invention are particularly effective in treating a variety of B-cell lymphomas, including low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small noncleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies bearing compatible tumor associated antigens.

B. Immune Disorder Therapies

Besides neoplastic disorders, the polypeptides of the instant invention are particularly effective in the treatment of autoimmune disorders or abnormal immune responses. In this regard, it will be appreciated that the polypeptide of the present invention may be used to control, suppress, modulate or eliminate unwanted immune responses to both external antigens and autoantigens. For example, in one embodiment, the antigen is an autoantigen. In another embodiment, the antigen is an allergan. In yet other embodiments, the antigen is an alloantigen or xenoantigen. Use of the disclosed modified polypeptides to reduce an immune response to alloantigens and xenoantigens is of particular use in transplantation, for example to inhibit rejection by a transplant recipient of a donor graft, e.g. a tissue or organ graft or bone marrow transplant. Additionally, suppression or elimination of donor T cells within a bone marrow graft is useful for inhibiting graft versus host disease.

In yet other embodiments the polypeptides of the present invention may be used to treat immune disorders that include, but are not limited to, allergic bronchopulmonary aspergillosis; Allergic rhinitis Autoimmune hemolytic anemia; Acanthosis nigricans; Allergic contact dermatitis; Addison's disease; Atopic dermatitis; Alopecia greata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cirrhosis; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; lupus nephritis; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus; Pemphigus foliaceus; Pemphigus vulgaris; Pigeon breeder's disease; Pneumonitis, hypersensitivity; Polyarteritis nodosa; Polymyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Scleroderma, Serum sickness; Sezary syndrome; Sjogren's syndrome; Stevens-Johnson syndrome; Still's disease; Subacute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis and Wiskott-Aldrich syndrome.

C Anti-Inflammatory Therapy

In yet other embodiments, the polypeptides of the present invention may be used to treat inflammatory disorders that are caused, at least in part, or exacerbated by inflammation, e.g., increased blood flow, edema, activation of immune cells (e.g., proliferation, cytokine production, or enhanced phagocytosis). Exemplary inflammatory disorders include those in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, mitochondria, apoptosis, adhesion molecules, etc.) are involved or are present in a given area or tissue in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories.

Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, Alzheimer's; severe asthma, atherosclerosis, cachexia, CHF-ischemia, and coronary restenosis; osteoarthritis, rheumatoid arthritis, fibrosis/radiation-induced or juvenile arthritis; acute and chronic infections (bacterial, viral and fungal); acute and chronic bronchitis, sinusitis, and other respiratory infections, including the common cold; acute and chronic gastroenteritis and colitis and Crohn's disease; acute and chronic cystitis and urethritis; acute respiratory distress syndrome; cystic fibrosis; acute and chronic dermatitis; psoriasis; acute and chronic conjunctivitis; acute and chronic serositis (pericarditis, peritonitis, synovitis, pleuritis and tendinitis); uremic pericarditis; acute and chronic cholecystis; acute and chronic vaginitis; stroke, inflammation of the brain or central nervous system caused by trauma, and ulcerative colitis; acute and chronic uveitis; drug reactions; diabetic nephropathy, and burns (thermal, chemical, and electrical). Other inflammatory disorders or conditions that can be prevented or treated with the antibodies or antigen-binding fragments of the invention include inflammation due to corneal transplantation, chronic obstructive pulmonary disease, hepatitis C, lymphoma, multiple myeloma, and osteoarthritis.

In another embodiment, the polypeptides of the invention can be used to prevent or treat neurodegenerative disorders, including, but not limited to Alzheimer's, stroke, and traumatic brain or central nervous system injuries. Additional neurodegenerative disorders include ALS/motor neuron disease, diabetic peripheral neuropathy, diabetic retinopathy, Huntington's disease, macular degeneration, and Parkinson's disease.

In prophylactic applications, pharmaceutical compositions comprising a polypeptide of the invention or medicaments are administered to a subject at risk for (or having and not yet exhibiting symptoms of) a disorder treatable with a polypeptide having an Fc region, for example, an immune system disorder, in an amount sufficient to eliminate or reduce the risk, lessen the severity, or delay the outset of the disorder, including biochemical, histologic and/or behavioral symptoms of the disorder, its complications and intermediate pathological phenotypes presenting during development of the disorder.

In therapeutic applications, compositions or medicaments are administered to a subject already suffering from such a disorder in an amount sufficient to cure, or at least partially arrest, the symptoms of the disorder (biochemical, histologic and/or behavioral), including its complications and intermediate pathological phenotypes in development of the disorder. The polypeptides of the invention are particularly useful for modulating the biological activity of a cell surface antigen that resides in the blood, where the disease being treated or prevented is caused at least in part by abnormally high or low biological activity of the antigen.

In some methods, administration of agent reduces or eliminates the immune disorder, for example, inflammation. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved.

It will be understood that the modified polypeptides of the invention can be used to treat a number of disorders not explicitly mentioned herein based on selection of the target molecule to which the polypeptide binds. It will be further recognized that any art recognized antibody or fusion protein may be modified according to the methods of the invention and used to treat a disorder for which it is indicated.

D. Methods of Administration

Polypeptides of the invention can be administered by startingeral, topical, intravenous, oral, intraarterial, intracranial, intraperitoneal, or intranasal means for prophylactic and/or therapeutic treatment. The term startingeral as used herein includes intravenous, intraarterial, intraperitoneal, intramuscular, subcutaneous, rectal or vaginal administration. The most typical route of administration of a protein drug is intravascular, subcutaneous, or intramuscular, although other routes can be effective. In some methods, agents are injected directly into a particular tissue where deposits have accumulated, for example intracranial injection. In some methods, antibodies are administered as a sustained release composition or device, such as a Medipad™ device. The protein drug can also be administered via the respiratory tract, e.g., using a dry powder inhalation device.

Effective doses of the compositions of the present invention, for the treatment of the above described conditions vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

For passive immunization with an antibody, the dosage ranges from about 0.0001 to 100 mg/kg, and more usually 0.01 to 20 mg/kg, of the host body weight.

For example dosages can be 1 mg/kg body weight or 10 mg/kg body weight or within the range of 1-10 mg/kg, preferably at least 1 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two polypeptides with different binding specificities are administered simultaneously, in which case the dosage of each polypeptide administered falls within the ranges indicated.

Polypeptides are usually administered on multiple occasions. Intervals between single dosages can be weekly, monthly or yearly. In some methods, dosage is adjusted to achieve a plasma antibody concentration of 1-1000 µg/ml and in some methods 25-300 µg/ml. Alternatively, polypeptides can be administered as a sustained release formulation, in which case less frequent administration is required. Dosage and frequency vary depending on the half-life of the polypeptide in the subject. In general, human antibodies show the longest half-life, followed by humanized antibodies, chimeric antibodies, and nonhuman antibodies. As discussed herein, the half-life also depends upon the particular mutation(s) present in the polypeptide.

The dosage and frequency of administration can vary depending on whether the treatment is prophylactic or therapeutic. In prophylactic applications, compositions containing the present antibodies or a cocktail thereof are administered to a subject not already in the disease state to enhance the subject's resistance. Such an amount is defined to be a "prophylactic effective dose." In this use, the precise amounts again depend upon the subject's state of health and general immunity, but generally range from 0.1 to 25 mg per dose, especially 0.5 to 2.5 mg per dose. A relatively low dosage is administered at relatively infrequent intervals over a long period of time. Some subjects continue to receive treatment for the rest of their lives.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the subject shows partial or complete amelioration of symptoms of disease. Thereafter, the patent can be administered a prophylactic regime.

Doses for nucleic acids encoding antibodies range from about 10 ng to 1 g, 100 ng to 100 mg, 1 µg to 10 mg, or 30-300 µg DNA per subject. Doses for infectious viral vectors vary from 10-100, or more, virions per dose.

One skilled in the art would be able, by routine experimentation, to determine what an effective, non-toxic amount of polypeptide would be for the purpose of treating a disorder. For example, a therapeutically active amount of a modified polypeptide may vary according to factors such as the disease stage (e.g., stage I versus stage IV tumor), age, sex, medical complications (e.g., immunosuppressed conditions or diseases) and weight of the subject, and the ability of the modified polypeptide to elicit a desired response in the subject. The dosage regimen may be adjusted to provide the optimum therapeutic response. For example, several divided doses may be administered daily, or the dose may be proportionally reduced as indicated by the exigencies of the therapeutic situation.

E. Monitoring of Treatment

Treatment of a subject suffering from a disease or disorder can be monitored using standard methods. Some methods entail determining a baseline value, for example, of an antibody level or profile in a subject, before administering a dosage of agent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the agent has achieved a desired response). If the value for immune response does not change significantly, or decreases, a negative treatment outcome is indicated.

In other methods, a control value (i.e., a mean and standard deviation) of level or profile is determined for a control population. Typically the individuals in the control population have not received prior treatment. Measured values of the level or profile in a subject after administering a therapeutic agent are then compared with the control value. A significant increase relative to the control value (e.g., greater than one standard deviation from the mean) signals a positive or sufficient treatment outcome. A lack of significant increase or a decrease signals a negative or insufficient treatment outcome. Administration of agent is generally continued while the level is increasing relative to the control value. As before, attainment of a plateau relative to control values is an indicator that the administration of treatment can be discontinued or reduced in dosage and/or frequency.

In other methods, a control value of the level or profile (e.g., a mean and standard deviation) is determined from a control population of individuals who have undergone treatment with a therapeutic agent and whose levels or profiles have plateaued in response to treatment. Measured values of levels or profiles in a subject are compared with the control value. If the measured level in a subject is not significantly different (e.g., more than one standard deviation) from the control value, treatment can be discontinued. If the level in a subject is significantly below the control value, continued administration of agent is warranted. If the level in the subject persists below the control value, then a change in treatment may be indicated.

In other methods, a subject who is not presently receiving treatment but has undergone a previous course of treatment is monitored for polypeptide levels or profiles to determine whether a resumption of treatment is required. The measured level or profile in the subject can be compared with a value previously achieved in the subject after a previous course of treatment. A significant decrease relative to the previous measurement (i.e., greater than a typical margin of error in repeat measurements of the same sample) is an indication that treatment can be resumed. Alternatively, the value measured in a subject can be compared with a control value (mean plus standard deviation) determined in a population of subjects after undergoing a course of treatment. Alternatively, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level (i.e., more than a standard deviation) is an indicator that treatment should be resumed in a subject.

The polypeptide profile following administration typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of polypeptide to a given antigen in the subject is made before administration, a second measurement is made soon thereafter to determine the peak polypeptide level, and one or more further measurements are made at intervals to monitor decay of polypeptide levels. When the level of polypeptide has declined to baseline or a predetermined percentage of the peak less baseline (e.g., 50%, 25% or 10%), administration of a further dosage of polypeptide is administered. In some methods, peak or subsequent measured levels less background are compared with reference levels previously determined to constitute a beneficial prophylactic or therapeutic treatment regime in other subjects. If the measured polypeptide level is significantly less than a reference level (e.g., less than the mean minus one standard deviation of the reference value in population of subjects benefiting from treatment) administration of an additional dosage of polypeptide is indicated.

Additional methods include monitoring, over the course of treatment, any art-recognized physiologic symptom (e.g., physical or mental symptom) routinely relied on by researchers or physicians to diagnose or monitor disorders.

F. Combination Therapy

Polypeptides of the invention can optionally be administered in combination with other agents (including any agent from Section VIII supra) that are known or determined to be effective in treating the disorder or condition in need of treatment (e.g., prophylactic or therapeutic). In addition, the polypeptides of the invention can be conjugated to a moiety that adds functionality to the polypeptide, e.g., (e.g., PEG, a tag, a drug, or a label).

It will further be appreciated that the polypeptides of the instant invention may be used in conjunction or combination with any chemotherapeutic agent or agents (e.g. to provide a combined therapeutic regimen) that eliminates, reduces, inhibits or controls the growth of neoplastic cells in vivo. Exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD adriamycin, bleomycin, vinblastine and dacarbazine), Ch1VPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas*, in HARRISON'S PRINCIPLES OF INTERNAL MEDICINE 1774-1788 (Kurt J. Isselbacher et al., eds., 13$^{th}$ ed. 1994) and V. T. DeVita et al., (1997) and the references cited therein for standard dosing and scheduling. These therapies can be used unchanged, or altered as needed for a particular patient, in combination with one or more modified polypeptides of the invention as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), Pro-MACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, carboplatin, cisplatin, etoposide and ifosfamide given alone or in combination. In relapsed or aggressive forms of certain neoplastic disorders the following protocols are often used: IMVP-16 (ifosfamide, methotrexate and etoposide), MIME (methyl-gag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the modified polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9$^{th}$ ed. 1996).

While the modified polypeptides may be administered as described herein, it must be emphasized that in other embodiments modified polypeptides may be administered to otherwise healthy patients as a first line therapy. In such embodiments the modified polypeptides may be administered to patients having normal or average red marrow reserves and/or to patients that have not, and are not, undergoing. As used herein, the administration of modified polypeptides in conjunction or combination with an adjunct therapy means the sequential, simultaneous, coextensive, concurrent, concomitant or contemporaneous administration or application of the therapy and the disclosed antibodies. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the present invention. Conversely, cytotoxin associated modified polypeptides could be administered intravenously followed by tumor localized external beam radiation. In yet other embodiments, the modified polypeptide may be administered concurrently with one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard it will be appreciated that the combination of the modified polypeptide and the chemotherapeutic agent may be administered in any order and within any time frame that provides a therapeutic benefit to the patient. That is, the chemotherapeutic agent and modified polypeptide may be administered in any order or concurrently. In selected embodiments the modified polypeptides of the present invention will be administered to patients that have previously undergone chemotherapy. In yet other embodiments, the modified polypeptides and the chemotherapeutic treatment will be administered substantially simultaneously or concurrently. For example, the patient may be given the modified antibody while undergoing a course of chemotherapy. In preferred embodiments the modified antibody will be administered within 1 year of any chemotherapeutic agent or treatment. In other preferred embodiments the modified polypeptide will be administered within 10, 8, 6, 4, or 2 months of any chemotherapeutic agent or treatment. In still other preferred embodiments the modified polypeptide will be administered within 4, 3, 2 or 1 week of any chemotherapeutic agent or treatment. In yet other embodiments the modified polypeptide will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

IX. PHARMACEUTICAL COMPOSITIONS

The therapeutic compositions of the invention include at least one of the polypeptides produced by a method described herein in a pharmaceutically acceptable carrier. A "pharmaceutically acceptable carrier" refers to at least one component of a pharmaceutical preparation that is normally used for administration of active ingredients. As such, a carrier may contain any pharmaceutical excipient used in the art and any form of vehicle for administration. The compositions may be, for example, injectable solutions, aqueous suspensions or solutions, non-aqueous suspensions or solutions, solid and liquid oral formulations, salves, gels, ointments, intradermal patches, creams, lotions, tablets, capsules, sustained release formulations, and the like. Additional excipients may include, for example, colorants, taste-masking agents, solubility aids, suspension agents, compressing agents, enteric coatings, sustained release aids, and the like.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Polypeptides can be administered in the form of a depot injection or implant preparation, which can be formulated in such a manner as to permit a sustained release of the active ingredient. An exemplary composition comprises polypeptide at 5 mg/mL, formulated in aqueous buffer consisting of 50 mM L-histidine, 150 mM NaCl, adjusted to pH 6.0 with HCl. An exemplary generic formulation buffer is 20 mM sodium citrate, pH 6.0, 10% sucrose, 0.1% Tween 80.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249:1527, 1990 and Hanes, *Advanced Drug Delivery Reviews* 28:97, 1997).

In general, the practice of the present invention employs, unless otherwise indicated, conventional techniques of chemistry, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

This invention is further illustrated by the following examples which should not be construed as limiting. The contents of all references, patents, and published patent applications cited throughout this application, as well as the figures and the sequence listing, are hereby incorporated by reference.

EXAMPLES

Example 1

Humanization of the B3F6 Antibody

For humanization of the B3F6 VL chain, the framework sequence gi-21669417 (BAC01733) was selected as the acceptor.

Sequence analysis revealed that FR residue 2 differs between the donor and acceptor (F in donor V in acceptor). The residue was identified as being important because it interacts with H93 (in CDR-L3), involved in binding peptide antigen.

The light chain environment around the F at position 2 was examined in the donor antibody. In one embodiment, the I at position 29 in donor DRL1 was changed to F. In another embodiment, the H at position 93 was left as H or changed to I or Y. In another embodiment, the H at position 93 was changed to W. In another embodiment, the H at position 93 was changed to I or Y.

An alignment of the light chain of donor murine B3F6, the acceptor, and the various humanized designs is shown in FIG. 1. The differences in FR amino acid residues and the positions of the changes made in the humanized form are bolded. Kabat numbers are indicated along the top of the alignment.

For humanization of the B3F6 VH chain, the framework sequence gi-14289106 (AAK57792) was selected as the acceptor. Sequence analysis revealed that FR residues 48, 67, 71, 73, 93, and 112 differed between donor and acceptor. With respect to position 48 this residue was found to be close to CDR-H2, which is not close to peptide antigen. Residue 67 was found to be close to CDR-H2, which is not close to peptide antigen. Residue 71 is known to be canonical and, therefore was classified as important (V in donor, R in acceptor). Residue 73 was found to be close to CDR-H2, which is not close to peptide antigen. With respect to residue 93 the residue was found to be an interface residue, but there is no obvious sidechain contact. Residue 112 was found to be an unusual human residue.

The heavy chain environment around V71 was examined in the donor antibody. The N at position 51 was changed to L in one embodiment. Also the N at position 51 was changed to I.

An alignment of the heavy chain of donor murine B3F6, the acceptor, and the various humanized designs is shown in FIG. 2. The differences in FR amino acid residues and the positions of the changes made in the humanized form are bolded. Kabat numbers are indicated along the top of the alignment.

Example 2

Humanization of the HP1/2 Antibody

For humanization of the murine HP1/2 VH domain (SEQ ID NO: 19), the human germline framework IGHV-1f (SEQ ID NO:20) was selected as acceptor. The murine HP1/2 antibody has an unusual canonical residue D94 (Kabat numbering) which interacts with residues F27, T32, and M34 of CDR-H1, M96 of CDR-H3 and A24 of FR1 as judged from the computational analysis of x-ray structure of murine HP1/2 Fab fragment.

Figure 4:
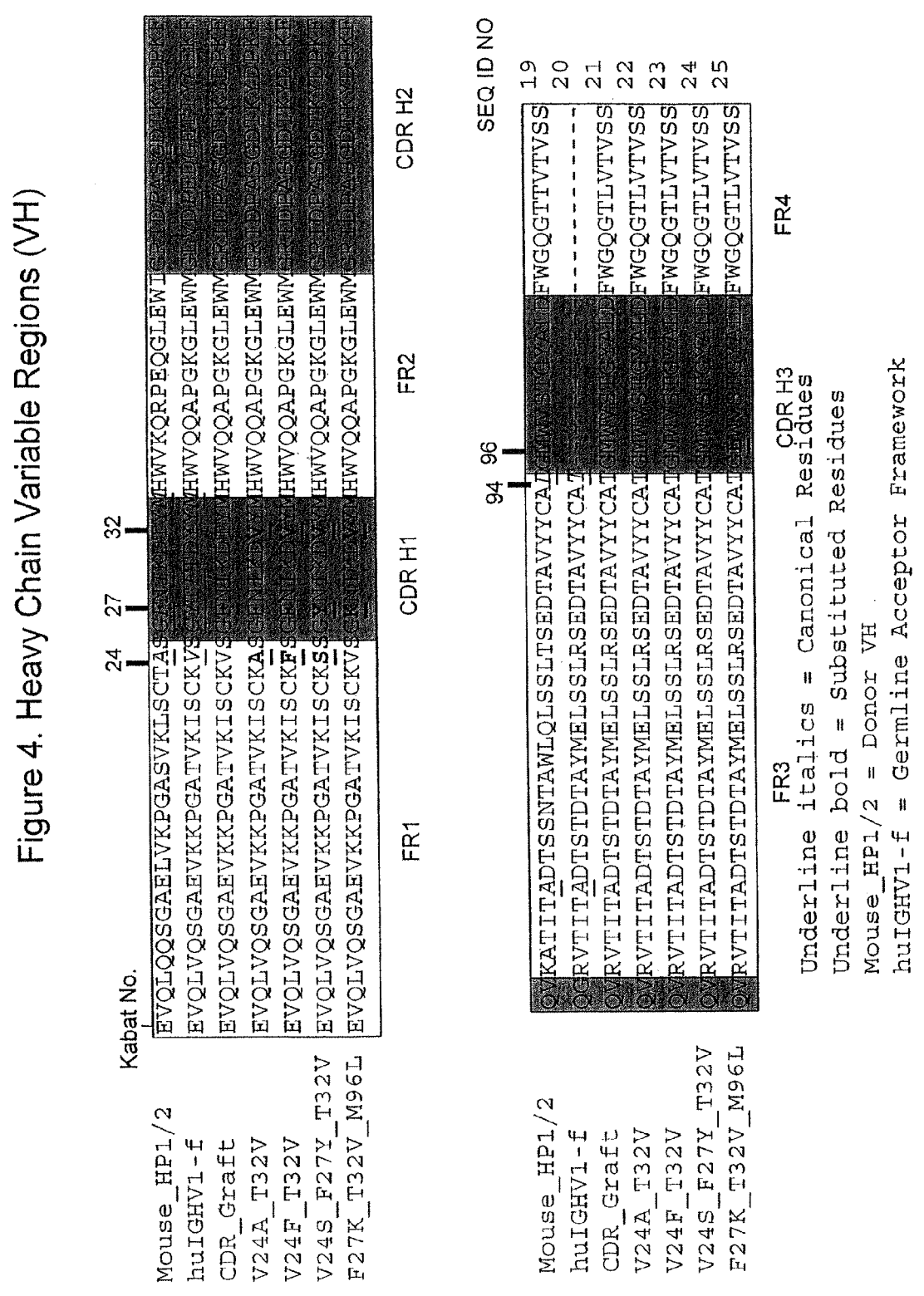

Sequence alignment analysis (see FIG. 4) indicated that human acceptor framework IGHV-1f has a threonine at position 94 in place of a murine aspartate residue. VH CDR graft (SEQ ID NO:21) was predicted to have different CDR-H1 and CDR-H3 conformations as compared to murine HP1/2 CDR-H1 and CDR-H3. The computational analysis of potential substitutions at CDR positions 27, 32, 34, and 96 and at position 24 in the framework revealed solution structures that maintained the conformations of CDR-H1 and CDR-H3 to allow for threonine in position 94.

Figure 6:
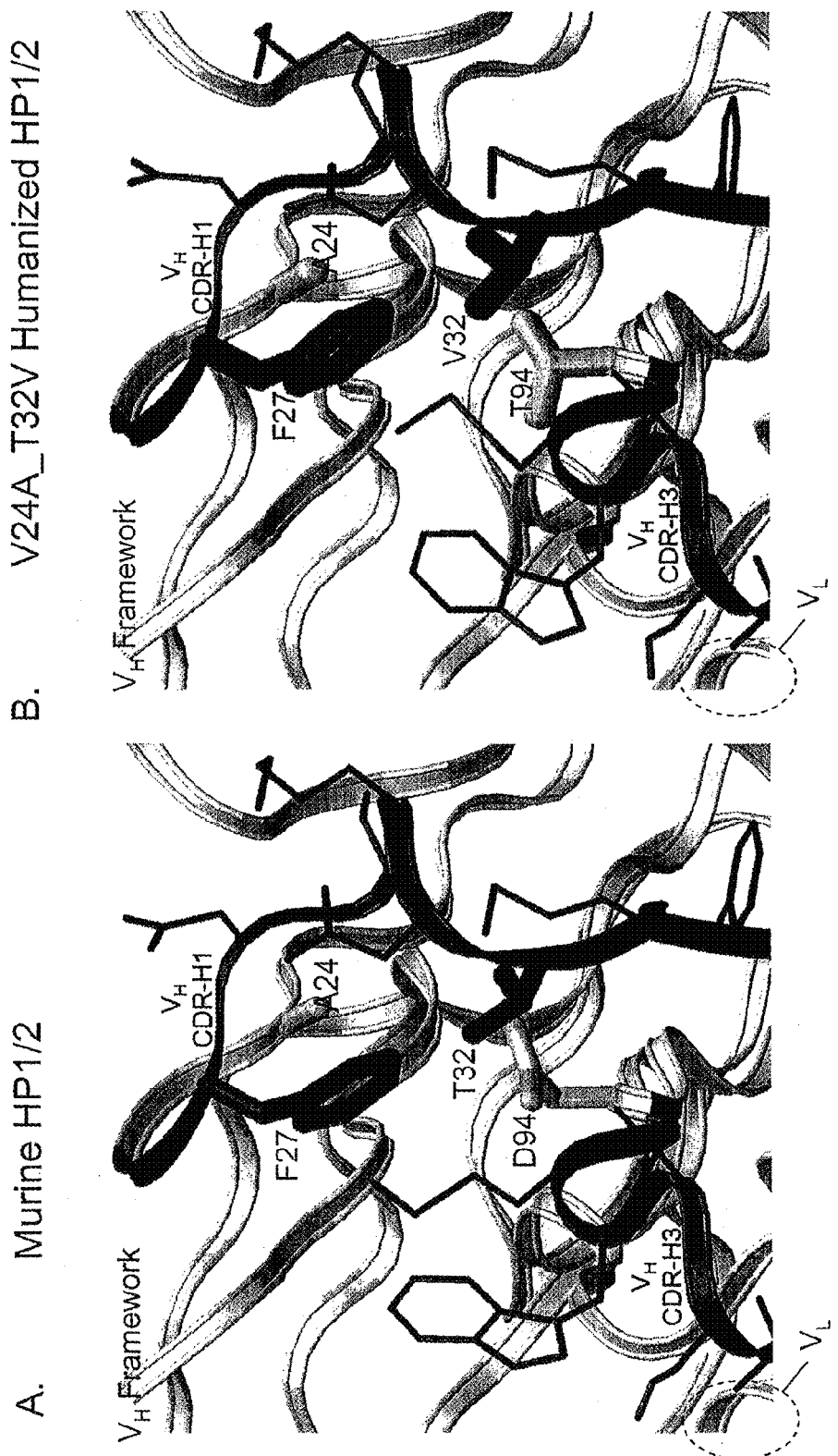
FIG. 6 panel A shows a three dimensional representation of light and heavy chains of a HP1/2 antibody molecule. The VH framework is shown in light ribbon, the VL framework is also in light ribbon but appears only at the bottom left corner, the VH CDR-H1 and CDR-H3 regions are in dark ribbon with dark thin stick sidechains, the CDR-H1 residues 27 and 32 are in thick dark stick, and the VH framework residues of importance 24 and 94 are in thick light stick. Panel B shows the V24A_T32V design.

In one embodiment, the V at position 24 was changed to A and the T at position 32 was changed to V, while the F at position 27, the M at position 34, and the M at position 96 were retained (V24A_T32V; SEQ ID NO:22). In a 3D model of this embodiment, the side chain of F at position 27 interacts with the side chain of A at position 24 and the non-polar portion of the T94 side chain interacts with V at position 32 and M at position 34. This interaction network puts the newly designed CDR-H1 in a conformation similar to that of donor murine CDR-H1. Tree-dimensional representations of the donor HP1/2 antibody and the V24A_T32V humanization design are depicted in FIG. 6.

In another embodiment, the V at position 24 was changed to F and the T at position 32 was changed to V, while the F at position 27, the M at position 34, and the M at position 96 were retained (V24F_T32V; SEQ ID NO:23). In a 3D model of this embodiment, the side chain of F at position 27 interacts with the side chain of F at position 24 and the non-polar portion of the T94 side chain interacts with V at position 32 and M at position 34. This interaction network puts the newly designed CDR-H1 in the conformation similar to donor murine CDR-H1.

In another embodiment, the V at position 24 was changed to S, the F at position 27 was changed to Y, and the T at position 32 was changed to V, while the M at position 34 and the M at position 96 were retained (V24S_F27Y_T32V; SEQ ID NO:24). In a 3D model of this embodiment, the side chain of Y at position 27 forms hydrogen bonds with side chain of S at position 24 and side chain of T at position 94, while the non-polar portion of the T94 side chain interacts with V at position 32. This interaction network puts the newly designed CDR-H1 in the conformation similar to donor murine CDR-H1.

In another embodiment, the F at position 27 was changed to K, the T at position 32 was changed to V, and the M at position 96 was changed to L, while the V at position 24 and the M at position 34 were retained (F27K_T32V_M96L; SEQ ID NO:25). In a 3D model of this embodiment, the side chain of K at position 27 forms hydrogen bonds with the side chain of T at position 94 as well as non-polar contacts with V at position 24, V at position 32, and L at position 96, while the non-polar portion of the T94 side chain interacts with M at position 34. This interaction network puts the newly designed CDR-H1 in the conformation similar to donor murine CDR-H1.

Computational analysis of the x-ray structure of murine HP1/2 and VL sequences (FIG. 5) revealed that the CDRs of the murine HP1/2 VL domain (SEQ ID NO:26) are compatible with the human germline acceptor framework B3 (SEQ ID NO:27), and therefore, a VL CDR graft (SEQ ID NO 10) was built (SEQ ID NO:28). Validity of this approach to the VL was demonstrated in a different humanization effort for the HP1/2 antibody.

Example 3

α4β1/mAb HP1/2Fab ELISA Binding Assay

HP1/2 Fab fragments of different VH humanization variants of Example 2 paired with VL CDR graft were expressed and their binding affinity for purified α4β1 VLA4 integrin were compared in an ELISA binding assay with a chimeric Fab that has murine VH and VL domains.

In this assay, 1 ug/ml of purified VLA4 (in 50 mM $NaHCO_3$ buffer (pH 9.2) containing 10 ug/ml BSA) was coated on a 96-well (100 ul/well) Corning Easy-wash plate and incubated overnight at 4° C. Following incubation, the plate was blocked with 150 ul/well of blocking buffer (50 mM Tris-HCl pH7.5, 150 mM NaCl and 2% Dry Milk) for 60 minutes at room temperature. The plated was then washed four times with TBS Washing buffer (50 mM Tris-HCl pH 7.5, 150 mM NaCl, 0.05% Tween-20). Dilutions of each HP1/2 Fab to be tested were prepared in binding buffer (TBS buffer containing 2% Dry Milk) and 100 ul of each dilution was added to the designated wells (100 ul of TBS assay buffer was used as blank control). The plate was then incubated for 60 minutes at room temperature, and then washed four times with TBS Washing buffer. The detection antibody (goat anti-human IgG HRP conjugate) was added at 100 ul/well and the plated was again incubated at room temperature for 60 minutes and washed four times with TBS Washing buffer beforeadding 100 ul/well HRP Substrate buffer and incubating another 30-60 minutes. To stop the reaction, 100 ul of 1 NH2SO4 was added to each well. The plate was read in a Molecular Devices ELISA plate reader at 450 nM, and the data was analyzed using Softmax software and EC50 values calculated by GraphPad Prism 4. The EC50 values observed for the test Fab fragments with VH and VL domains are tabulated in

TABLE 2

VLA-4 Binding Affinity of Chimeric and Humanized HP1/2 FAbs

| Fab | VH | VL | EC50 (nM) |
| --- | --- | --- | --- |
| Chimeric | SEQ ID NO: 19 | SEQ ID NO: 26 | 0.052 |
| CDR-Graft | SEQ ID NO: 21 | SEQ ID NO: 28 | 1.1 |
| V24A_T32V | SEQ ID NO: 22 | SEQ ID NO: 28 | 0.066 |
| V24F_T32V | SEQ ID NO: 23 | SEQ ID NO: 28 | 0.13 |
| V24S_F27Y_T32V | SEQ ID NO: 24 | SEQ ID NO: 28 | 0.032 |
| F27Y_T32V_M96L | SEQ ID NO: 25 | SEQ ID NO: 28 | 0.14 |

EQUIVALENTS

For one skilled in the art, using no more than routine experimentation, there are many equivalents to the specific embodiments of the invention described herein. Such equivalents are intended to be encompassed by the following claims.

What is claimed is:

1. A polypeptide comprising the humanized Ig variable region which comprises a) variable region framework (FR) amino acid residues from a human acceptor Ig variable region and b) complementary determining regions (CDRs) from a non-human donor Ig variable region, produced by a method of humanizing an immunoglobulin (Ig) variable region, the method comprising, i) providing data which allows prediction of a 3-D conformation of at least one CDR;
   ii) identifying which FR amino acid residues are predicted to affect the 3-D conformation of the at least one CDR;
   iii) identifying at least one candidate donor CDR amino acid residue for substitution with an elected amino acid residue, wherein the elected amino acid residue conformationally accommodates a FR amino acid residue difference between the donor Ig variable region and the acceptor Ig variable region without affecting the CDR conformation; and
   iv) substituting the at least one candidate donor CDR amino acid residue with the elected amino acid residue, such that the immunoglobulin variable region is humanized, and
   v) expressing a polypeptide comprising the humanized Ig variable region, wherein the polypeptide binds to an antigen with an affinity that is greater than or not substantially changed as compared to the affinity of the donor Ig variable region for the antigen.

2. The polypeptide of claim 1, wherein step (iii) further comprises identifying at least one candidate acceptor FR residue for substitution with a second elected amino acid residue, wherein the second elected amino acid residue conformationally accommodates a FR amino acid residue difference between the donor Ig variable region and the acceptor Ig variable region without affecting the CDR conformation.

3. The polypeptide of claim 2, wherein step (iv) further comprises substituting the at least one candidate acceptor FR residue with the second elected amino acid residue.

4. The polypeptide of claim 1, wherein step (i) comprises evaluating a 3-dimensional (3D) structure of the non-human donor Ig variable region.

5. The polypeptide of claim 1, wherein step (i) comprises evaluating x-ray diffraction data of the non-human donor Ig variable region.

6. The polypeptide of claim 1, wherein step (i) comprises evaluating a computer generated model of the non-human donor Ig variable region.

7. A polypeptide comprising the humanized Ig variable region comprising a) variable framework regions (FRs) from a human acceptor Ig variable region and b) complementarity determining regions (CDRs) from a non-human donor Ig variable region produced by a method of humanizing an immunoglobulin (Ig) variable region, the method comprising,
 i) identifying framework region (FR) amino acids which differ between the acceptor Ig variable region and the donor Ig variable region;
 ii) identifying amino acids adjacent to the FR amino acid(s) identified in step i)
 iii) identifying at least one candidate amino acid residue from the amino acids identified in step ii) for substitution with an elected amino acid residue which conformationally accommodates the FR amino acid(s) identified in step i) (a); and
 iv) substituting the candidate amino acid residue with the elected amino acid residue such that the humanized Ig variable region is designed, and
 v) expressing a polypeptide comprising the humanized Ig variable region,
 wherein the polypeptide binds to an antigen with an affinity that is greater than or not substantially changed as compared to the affinity of the donor Ig variable region for the antigen.

8. The polypeptide of claim 7, where the FR amino acid identified in step i) is a canonical FR residue.

9. The polypeptide of claim 7, wherein the amino acid identified in step ii) is immediately adjacent to the FR amino acid identified in step i).

10. The polypeptide of claim 7, wherein the amino acid identified in step ii) is within about 4 Å of 3-D space from the FR amino acid identified in step i).

11. The polypeptide of claim 7, wherein the elected amino acid residue is identified by side chain repacking.

12. The polypeptide of claim 11, wherein the elected amino acid residue is selected from all possible rotamers of all possible amino acids.

13. The polypeptide of claim 11, wherein the elected amino acid residue is selected from a subset of all possible rotamers of all possible amino acids.

14. The polypeptide of claim 7, wherein the elected amino acid residue is identified as an amino acid that is most commonly present at the position of the candidate amino acid within a set of homologous antibody variable region sequences having the same FR amino acid as the FR amino acid identified in step i).

15. The polypeptide of claim 7, wherein the subset comprises all possible rotamers of amino acids that are commonly present at the position of the candidate amino acid within a set of homologous antibody variable region sequences having the same FR amino acid as the FR amino identified in step i).

16. A polypeptide comprising the humanized Ig variable region which comprises a) variable region framework (FR) amino acid residues from a human acceptor Ig variable region and b) complementarity determining region CDRs from a non-human donor Ig variable region produced by a method of humanizing a humanized Ig variable region, the method comprising,
 i) selecting a non-human donor Ig variable region;
 ii) selecting an acceptor Ig variable region;
 iii) identifying at least one candidate CDR amino acid residue in the donor Ig variable region for substitution with an elected amino acid residue, where:
  (a) the candidate CDR amino acid residue is immediately adjacent to an FR amino acid residue of the acceptor Ig variable region; or
  (b) the candidate CDR amino acid residue is predicted to have a side chain atom whose Van der Waals surface is within about 4 Å of an FR amino acid residue of the acceptor Ig variable region in a 3D immunoglobulin model and is predicted to interact with at least one variable region FR amino acid residue of the humanized Ig chain; and
 iv) substituting the candidate CDR amino acid residue with the elected amino acid residue,
 such that the humanized Ig variable region is designed, and
 v) expressing a polypeptide comprising the humanized Ig variable region,
 wherein the polypeptide binds to an antigen with an affinity that is greater than or not substantially changed as compared to the affinity of the donor Ig variable region for the antigen.

17. The polypeptide of claim 16, wherein step iii) further comprises identifying at least one candidate FR amino acid residue in the acceptor Ig variable region for substitution with a second elected amino acid residue, where:
 (a) the candidate FR amino acid residue is immediately adjacent to a CDR amino acid residue of the donor Ig variable region; or
 (b) the candidate FR amino acid residue is predicted to have a side chain atom whose Van der Waals surface is within about 4 Å of a CDR amino acid residue of the donor Ig variable region in a 3D immunoglobulin model and is predicted to interact with at least one variable region CDR amino acid residue of the humanized Ig chain; and
 wherein step iv) further comprises substituting the candidate FR amino acid residue with the elected amino acid residue,
 such that the humanized Ig variable region is designed, and
 wherein the substitution of the candidate FR amino acid residue with the elected amino acid residue conformationally accommodates the CDR amino acid residue.

18. The polypeptide of any one of claim 1, 7 or 16, wherein the humanized Ig variable region is present in an intact antibody molecule.

19. The polypeptide of any one of claim 1, 7 or 16, wherein the humanized Ig variable region is present in a fragment of an antibody molecule.

20. The polypeptide of any one of claim 1, 7 or 16, wherein the humanized Ig variable region is present in a molecule selected from the group consisting of: an antibody, an antibody light chain (VL), an antibody heavy chain (VH), a single chain antibody (scFv), a F(ab')2 fragment, a Fab fragment, an Fd fragment, and a single domain fragment.

21. The polypeptide of any one of claim 1, 7 or 16, wherein the humanized Ig variable region is a light chain variable region.

22. The polypeptide of any one of claim 1, 7 or 16, wherein the humanized Ig variable region is a heavy chain variable region.

23. The polypeptide of any one of claim 1, 7 or 16, wherein the humanized Ig variable region comprises at least one variable region FR amino acid substitution.

24. The polypeptide of any one of claim 1, 7 or 16, wherein the acceptor Ig variable region is derived from a human antibody.

25. The polypeptide of any one of claim 1, 7 or 16, wherein the acceptor Ig variable region is derived from a human consensus sequence.

26. The polypeptide of any one of claim 1, 7 or 16, wherein the acceptor Ig variable region is derived from a human germline sequence.

27. The polypeptide of any one of claim 1, 7 or 16, wherein in the method is repeated at least one time.

28. The polypeptide of any one of claim 1, 7 or 16, wherein one or more of steps (i)-(iv) in the method is conducted in silico.

29. The polypeptide of any one of claim 1, 7 or 16, wherein the polypeptide is expressed in an expression system selected from the group consisting of: an acellular extract expression system, a phage display expression system, a prokaryotic cell expression system, and a eukaryotic cell expression system.

30. The polypeptide of any one of claim 1, 7 or 16, wherein the non-human donor Ig variable region is from a mouse antibody.

31. The polypeptide of any one of claim 1, 7 or 16, wherein the non-human donor Ig variable region is from a primate antibody.

32. A pharmaceutical composition comprising the polypeptide of any one of claim 1, 7, or 16.

* * * * *

SEQUENCE LISTING

<160> NUMBER OF SEQ ID NOS: 32

<210> SEQ ID NO 1
<211> LENGTH: 188
<212> TYPE: PRT
<213> ORGANISM: Homo sapiens

<400> SEQUENCE: 1

Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Pro Ala Ile Arg Pro Arg Ser Ser
    50                  55                  60

Gln Arg Val Pro Pro Met Gly Ile Gln His Ser Lys Glu Leu Asn Arg
65                  70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
            180                 185

<210> SEQ ID NO 2
<211> LENGTH: 188
<212> TYPE: PRT
<213> ORGANISM: Homo sapiens

<400> SEQUENCE: 2

Met Asp Cys Arg Lys Met Val Arg Phe Ser Tyr Ser Val Ile Trp Ile
1               5                   10                  15

Met Ala Ile Ser Lys Ala Phe Glu Leu Gly Leu Val Ala Gly Leu Gly
            20                  25                  30

His Gln Glu Phe Ala Arg Pro Ser Arg Gly Asp Leu Ala Phe Arg Asp
        35                  40                  45

Asp Ser Ile Trp Pro Gln Glu Pro Ala Ile Arg Pro Arg Ser Ser
    50                  55                  60

Gln Arg Val Leu Pro Met Gly Ile Gln His Ser Lys Glu Leu Asn Arg
65                  70                  75                  80

Thr Cys Cys Leu Asn Gly Gly Thr Cys Met Leu Glu Ser Phe Cys Ala
                85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

```
Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Ala Gly Ile Cys Leu Ser Ile Gln Ser Tyr Tyr
            180                 185

<210> SEQ ID NO 3
<211> LENGTH: 112
<212> TYPE: PRT
<213> ORGANISM: Mus musculus

<400> SEQUENCE: 3

Asp Phe Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 4
<211> LENGTH: 112
<212> TYPE: PRT
<213> ORGANISM: Homo sapiens

<400> SEQUENCE: 4

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 5
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 5
```

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110
```

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 6

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Ile Val Pro Leu Thr Phe Gly Gln Gly Thr Lys Leu Glu Ile Lys
            100                 105                 110
```

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 7

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Phe Gln Gly
            85                  90                  95

Ser Tyr Val Pro Leu Thr Phe Gly Gln Gly Thr Lys Leu Glu Ile Lys
            100                 105                 110

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 8

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser Trp Val Pro Leu Thr Phe Gly Gln Gly Thr Lys Leu Glu Ile Lys
            100                 105                 110

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 9

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Phe Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser Tyr Val Pro Leu Thr Phe Gly Gln Gly Thr Lys Leu Glu Ile Lys
            100                 105                 110

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 10
```

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Phe Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Ile Val Pro Leu Thr Phe Gly Gln Gly Thr Lys Leu Glu Ile Lys
            100                 105                 110

<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 11

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Phe Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 12

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser His Val Pro Leu Thr Phe Gly Gln Gly Thr Lys Leu Glu Ile Lys
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 13

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser His Val His Ser
            20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser Trp Val Pro Leu Thr Phe Gly Gln Gly Thr Lys Leu Glu Ile Lys
            100                 105                 110

<210> SEQ ID NO 14
<211> LENGTH: 119
<212> TYPE: PRT
<213> ORGANISM: Mus musculus

<400> SEQUENCE: 14

Gln Val Gln Leu Gln Gln Val Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
            35                  40                  45

Gly Glu Asn Asp Pro Ser Asn Gly Arg Thr Asn Tyr Asn Glu Lys Phe
    50                  55                  60

Lys Asn Lys Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
            85                  90                  95

Ser Arg Gly Pro Asn Tyr Phe Tyr Ser Met Asp Tyr Trp Gly Gln Gly
            100                 105                 110

Thr Ser Val Thr Val Ser Ser
        115

<210> SEQ ID NO 15
<211> LENGTH: 119
<212> TYPE: PRT
<213> ORGANISM: Homo sapiens

<400> SEQUENCE: 15

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Phe Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Asp Thr Ala Ile Asp Ala Phe Asp Ile Trp Gly Gln Gly
            100                 105                 110

Thr Met Val Thr Val Cys Ser
        115

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 16

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Glu Asn Asp Pro Ser Asn Gly Arg Thr Asn Tyr Asn Glu Lys Phe
    50                  55                  60

Lys Asn Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro Asn Tyr Phe Tyr Ser Met Asp Tyr Trp Gly Gln Gly
            100                 105                 110

Thr Met Val Thr Val Cys Ser
        115

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 17

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Glu Leu Asp Pro Ser Asn Gly Arg Thr Asn Tyr Asn Glu Lys Phe
    50                  55                  60

Lys Asn Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro Asn Tyr Phe Tyr Ser Met Asp Tyr Trp Gly Gln Gly
            100                 105                 110

Thr Met Val Thr Val Cys Ser
            115

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 18

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile His Trp Val Arg Gln Ala Pro Gly Gln Gly Leu Glu Trp Met
            35                  40                  45

Gly Glu Ile Asp Pro Ser Asn Gly Arg Thr Asn Tyr Asn Glu Lys Phe
        50                  55                  60

Lys Asn Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro Asn Tyr Phe Tyr Ser Met Asp Tyr Trp Gly Gln Gly
            100                 105                 110

Thr Met Val Thr Val Cys Ser
            115

<210> SEQ ID NO 19
<211> LENGTH: 121
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 19

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
                20                  25                  30

Tyr Met His Trp Val Lys Gln Arg Pro Glu Gln Gly Leu Glu Trp Ile
            35                  40                  45

Gly Arg Ile Asp Pro Ala Ser Gly Asp Thr Lys Tyr Asp Pro Lys Phe
        50                  55                  60

Gln Val Lys Ala Thr Ile Thr Ala Asp Thr Ser Ser Asn Thr Ala Trp
65                  70                  75                  80

Leu Gln Leu Ser Ser Leu Thr Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Thr Val Thr Val Ser Ser

```
                        115                 120

<210> SEQ ID NO 20
<211> LENGTH: 98
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 20

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 21

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Ser Gly Asp Thr Lys Tyr Asp Pro Lys Phe
    50                  55                  60

Gln Val Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Met Trp Val Ser Thr Gly Tyr Ala Leu Asp Phe Trp Gly
            100                 105                 110

Gln Gly Thr Leu Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 22

Glu Val Gln Leu Val Gln Ser Gly Ala Glu Val Lys Lys Pro Gly Ala
```

```
                1               5                  10                 15
Thr Val Lys Ile Ser Cys Lys Ala Ser Gly Phe Asn Ile Lys Asp Val
            20                  25                 30

Tyr Met His Trp Val Gln Gln Ala Pro Gly Lys Gly Leu Glu Trp Met
        35                  40                  45

Gly Arg Ile Asp Pro Ala Ser Gly Asp Thr Lys Tyr Asp Pro Lys Phe
    50                  55                  60

Gln Val Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Met Trp Val Ser Thr Gly Tyr Ala Leu Asp Phe Trp Gly
            100                 105                 110

Gln Gly Thr Leu Val Thr Val Ser Ser
        115                 120

<210> SEQ ID NO 23
<211> LENGTH: 121
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 23

Glu Val Gln Leu Val Gln Ser Gly Ala Glu Val Lys Lys Pro Gly Ala
1               5                   10                  15

Thr Val Lys Ile Ser Cys Lys Phe Ser Gly Phe Asn Ile Lys Asp Val
            20                  25                  30

Tyr Met His Trp Val Gln Gln Ala Pro Gly Lys Gly Leu Glu Trp Met
        35                  40                  45

Gly Arg Ile Asp Pro Ala Ser Gly Asp Thr Lys Tyr Asp Pro Lys Phe
    50                  55                  60

Gln Val Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Met Trp Val Ser Thr Gly Tyr Ala Leu Asp Phe Trp Gly
            100                 105                 110

Gln Gly Thr Leu Val Thr Val Ser Ser
        115                 120

<210> SEQ ID NO 24
<211> LENGTH: 121
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 24

Glu Val Gln Leu Val Gln Ser Gly Ala Glu Val Lys Lys Pro Gly Ala
1               5                   10                  15

Thr Val Lys Ile Ser Cys Lys Ser Ser Gly Tyr Asn Ile Lys Asp Val
            20                  25                  30

Tyr Met His Trp Val Gln Gln Ala Pro Gly Lys Gly Leu Glu Trp Met
        35                  40                  45

Gly Arg Ile Asp Pro Ala Ser Gly Asp Thr Lys Tyr Asp Pro Lys Phe
    50                  55                  60
```

```
Gln Val Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Met Trp Val Ser Thr Gly Tyr Ala Leu Asp Phe Trp Gly
            100                 105                 110

Gln Gly Thr Leu Val Thr Val Ser Ser
        115                 120
```

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 25

```
Glu Val Gln Leu Val Gln Ser Gly Ala Glu Val Lys Lys Pro Gly Ala
 1               5                  10                  15

Thr Val Lys Ile Ser Cys Lys Val Ser Gly Lys Asn Ile Lys Asp Val
            20                  25                  30

Tyr Met His Trp Val Gln Gln Ala Pro Gly Lys Gly Leu Glu Trp Met
        35                  40                  45

Gly Arg Ile Asp Pro Ala Ser Gly Asp Thr Lys Tyr Asp Pro Lys Phe
    50                  55                  60

Gln Val Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Leu Trp Val Ser Thr Gly Tyr Ala Leu Asp Phe Trp Gly
            100                 105                 110

Gln Gly Thr Leu Val Thr Val Ser Ser
        115                 120
```

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 26

```
Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Thr Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Tyr
                 85                  90                  95

Thr Phe Gly Gly Gly Thr Lys Leu Glu Ile Lys
            100                 105
```

```
<210> SEQ ID NO 27
<211> LENGTH: 101
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 28

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Thr Asn Asp
            20                  25                  30

Val Ala Trp Tyr Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Ser Ser Pro Tyr
                85                  90                  95

Thr Phe Gly Gln Gly Thr Lys Val Glu Ile Lys
            100                 105

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Ser Gly Gly Gly Ser Gly Gly Gly Gly Ser Gly
1               5                   10                  15

Gly Gly Gly Ser
            20
```

```
<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Gly Ser Ser Gly Gly Gly Ser Gly Gly
1               5                   10

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Gly Gly Ser Gly Gly Gly Gly Ser Gly Gly Gly Gly Ser Gly
1               5                   10                  15

Gly Gly Ser Gly Gly Gly Ala Ser
            20                  25
```